US011172888B2

(12) United States Patent
Nadkarni

(10) Patent No.: US 11,172,888 B2
(45) Date of Patent: Nov. 16, 2021

(54) OPTICAL BLOOD-COAGULATION SENSOR

(71) Applicant: Seemantini K. Nadkarni, Cambridge, MA (US)

(72) Inventor: Seemantini K. Nadkarni, Cambridge, MA (US)

(73) Assignee: THE GENERAL HOSPITAL CORPORATION, Boston, MA (US)

( * ) Notice: Subject to any disclaimer, the term of this patent is extended or adjusted under 35 U.S.C. 154(b) by 433 days.

(21) Appl. No.: 14/653,434

(22) PCT Filed: Dec. 19, 2013

(86) PCT No.: PCT/US2013/076470
§ 371 (c)(1),
(2) Date: Jun. 18, 2015

(87) PCT Pub. No.: WO2014/100378
PCT Pub. Date: Jun. 26, 2014

(65) Prior Publication Data
US 2015/0305681 A1 Oct. 29, 2015

Related U.S. Application Data

(60) Provisional application No. 61/739,167, filed on Dec. 19, 2012.

(51) Int. Cl.
*A61B 5/00* (2006.01)
*G01N 33/49* (2006.01)
(Continued)

(52) U.S. Cl.
CPC ........ *A61B 5/6898* (2013.01); *A61B 5/02028* (2013.01); *A61B 5/15* (2013.01);
(Continued)

(58) Field of Classification Search
CPC ..... A61B 5/6898; A61B 5/02028; A61B 5/15; A61B 5/7214; A61B 5/7246;
(Continued)

(56) References Cited

U.S. PATENT DOCUMENTS 4,252,536 A 2/1981 Kishimoto et al.
4,913,547 A * 4/1990 Moran ............... G01B 9/02067
356/489
(Continued)

FOREIGN PATENT DOCUMENTS

JP 2000055911 A 2/2000
JP 2002055109 A 2/2002
(Continued)

OTHER PUBLICATIONS

Chin-Lung Yang, Point-of-care Testing of Portable Blood Coagulation Detectors Using Optical Sensors, 12. Jan. 2012, 33(3), pp. 319-324.*
(Continued)

*Primary Examiner* — Sean P Dougherty
*Assistant Examiner* — Kyle W. Kretzer
(74) *Attorney, Agent, or Firm* — Quarles & Brady LLP

(57) ABSTRACT

Hand-held optical thromboelastographic sensor and method of using the same for simultaneous assessment of multiple parameters of blood coagulation at a point-of-care. The sensor includes an optical system registering laser speckle intensity associated with a stationary blood sample and data-processing circuitry programmed to derive the multiple parameters from speckle intensity. The circuitry may be part of a mobile device configured to operate without communication with a central server and/or data storage.

11 Claims, 10 Drawing Sheets

(51) Int. Cl.
*G01N 21/47* (2006.01)
*A61B 5/02* (2006.01)
*A61B 5/15* (2006.01)
*G01N 21/51* (2006.01)

(52) U.S. Cl.
CPC .......... *A61B 5/7214* (2013.01); *A61B 5/7246* (2013.01); *G01N 21/4788* (2013.01); *G01N 21/51* (2013.01); *G01N 33/4905* (2013.01); *A61B 2560/0425* (2013.01); *G01N 2021/479* (2013.01); *G01N 2201/0221* (2013.01)

(58) Field of Classification Search
CPC ....... A61B 2560/0425; G01N 21/4788; G01N 21/51; G01N 33/4905; G01N 2201/0221; G01N 2021/479
See application file for complete search history.

(56) References Cited

U.S. PATENT DOCUMENTS

| | | | | |
|---|---|---|---|---|
| 4,913,550 | A * | 4/1990 | Montgomery | G01H 9/002 356/502 |
| 5,020,904 | A * | 6/1991 | McMahan, Jr. | G01B 11/162 356/35.5 |
| 5,096,669 | A * | 3/1992 | Lauks | B01L 3/502707 204/403.02 |
| 5,789,664 | A * | 8/1998 | Neel | G01N 11/06 356/39 |
| 6,066,243 | A * | 5/2000 | Anderson | G16H 40/63 422/82.01 |
| 6,084,660 | A * | 7/2000 | Shartle | G01N 33/558 356/39 |
| 7,276,376 | B2 | 10/2007 | Katayama et al. | |
| 7,782,458 | B2 | 8/2010 | Snabre et al. | |
| 8,772,039 | B2 | 7/2014 | Nadkarni | |
| 2003/0098352 | A1* | 5/2003 | Schnee | G06K 7/10732 235/472.01 |
| 2004/0152989 | A1* | 8/2004 | Puttappa | A61B 5/14532 600/473 |
| 2004/0175296 | A1 | 9/2004 | Opalsky et al. | |
| 2005/0275836 | A1* | 12/2005 | Feldchtein | G01N 21/4795 356/243.1 |
| 2006/0110283 | A1 | 5/2006 | Fish | |
| 2007/0138284 | A1* | 6/2007 | Giordano | H04N 1/02865 235/454 |
| 2008/0234586 | A1* | 9/2008 | Tearney | A61B 5/0059 600/479 |
| 2009/0091741 | A1 | 4/2009 | Dogariu | |
| 2010/0248278 | A1 | 9/2010 | Pouteau et al. | |
| 2011/0014640 | A1 | 1/2011 | Yamamoto et al. | |
| 2011/0104738 | A1 | 5/2011 | Forsell | |
| 2012/0252127 | A1* | 10/2012 | Gregor | G01N 21/82 436/69 |
| 2012/0282139 | A1 | 11/2012 | Makino et al. | |

FOREIGN PATENT DOCUMENTS

| | | | | |
|---|---|---|---|---|
| JP | 2007175416 | A | | 7/2007 |
| RU | 2336525 | C2 | | 10/2008 |
| WO | 9201065 | A1 | | 1/1992 |
| WO | 2006065739 | A2 | | 6/2006 |
| WO | WO 2010105197 | A2 | * | 9/2010 ........... A61B 5/0059 |
| WO | WO-2010105197 | A2 | * | 9/2010 ........... A61B 5/0059 |
| WO | 2012/161960 | | | 11/2012 |

OTHER PUBLICATIONS

Erick Sarmineto-Gomez, A dynamical light scattering technique and its application in viscoelastic networks in soft matter, 2011, Proc. of SPIE, vol. 8011, pp. 1-9 (Year: 2011).*

Erick Sarmiento-Gomez, Julian Masasue Galvan-Miyoshi, Rolando Castillo, "A dynamical light scattering technique and its application in viscoelastic networks in soft matter," Proc. SPIE 8011, 22nd Congress of the International Commission for Optics: Light for the Development of the World, 801178 (Year: 2011).*
[item U continued] (Nov. 2, 2011); https://doi.org/10.1117/12.902163 (Year: 2011).*
Ganter, Michael T. MD*; Hofer, Christoph K. MD† Coagulation Monitoring: Current Techniques and Clinical Use of Viscoelastic Point-of-Care Coagulation Devices, Anesthesia & Analgesia: May 2008—vol. 106—Issue 5—p. 1366-1375 doi: 10.1213/ane.0b013e318168b367 (Year: 2008).*
The International Search Report and Written Opinion as dated May 7, 2014 for International Application No. PCT/US2013/076470.
Bleakly, et al., Disseminated Intravascular Coagulation Due to IgM-Mediated Autoimmune Hemolytic Anemia, Pediatr Blood Cancer, 2011, 57:329-331.
Devine, et al., Postoperative Acquired Coagulopathy: A Pilot Study to Determine the Impact on Clinical and Economic Outcomes, Pharmacotherapy, 2010, 30:994-1003 [Abstract Only].
Draijer, et al., Review of Laser Speckle Contrast Techniques for Visualizing Tissue Perfusion, Lasers Med. Sci., 2009, 24:639-651.
Faivre, et al., Coagulation Dynamics of a Blood Sample by Multiple Scattering Analysis, Journal of Biomedical Optics, 2011, 16(5):057001-1 thru 057001-9.
Genter. et al., Coagulation Monitoring: Current Techniques and Clinical Use of Viscoelastic Point-of-Care Coagulation Devices, Anesth. Analg., 2008, 106:1366-1375.
Goodeve, et al., Haemophilia A and von Willebrand's Disease, Haemophilia, 2010, 16(Suppl.5):79-84.
Hajjarian, et al., Intravascular Laser Speckle Imaging Catheter for the Mechanical Evaluation of the Arterial Wall, Journal of Biomedical Optics, 2011, 16(2):026005-1 thru 026005-7.
Hajjarian, et al., Evaluating the Viscoelastic Properties of Tissue from Laser Speckle Fluctuations, Scientific Reports, 2012, 2:316, pp. 1-8.
Lippi, et al., Inherited Disorders of Blood Coagulation, Annals of Medicine, 2012, 44:405-418.
Liu, et al., The Mechanical Properties of Single Fibrin Fibers, Journals of Thrombosis and Haemostasis, 2010, 8:1030-1036.
Nadkarni, et al., Characterization of Atherosclerotic Plaques by Laser Speckle Imaging, Circulation, 2005, 112:885-892.
Nadkarni, et al., Measurement of Fibrous Cap Thickness in Atherosclerotic Plaques by Spatiotemporal Analysis of Laser Speckle Images, Journal of Biomedical Optics, 2006, 11(2):21006-1 thru 021006-8.
Nadkarni, et al., Evaluation of Collagen in Atherosclerotic Plaques: The Use of Two Coherent Laser-Based Imaging Methods, Lasers Med. Sci., 24(3):439-445.
Piederriere, et al., Particle Aggregation Monitoring by Speckle Size Measurement; Application to Blood Platelets Aggregation, Optics Express, 2004, 12(19):4596-4601.
Piederriere, et al., Evaluation of Blood Plasma Coagulation Dynamics by Speckle Analysis, Journal of Biomedical Optics, 2004, 9(2):408-412.
Tripodi, et al., The Coagulopathy of Chronic Liver Disease, New England Journal of Medicine, 2011, 365:147-156.
Tripodi, et al., Hypercoagulability in Cirrhosis: Causes and Consequences, Journal of Thrombosis and Haemostasis, 2011, 9:1713-1723.
Vasileidis, et al., First Diagnosis of Factor XI Deficiency in a Patient with Subarachnoid Haemorrhage, Blood Coagul Fibrinolysis, 2009, 20(4):309-313.
PCT International Search Report and Written Opinion, PCT/US2012/037115, dated Aug. 2, 2012, 9 pages.
Hajjarian, et al., Measurement of Bulk Mechanical Properties of Tissue Using Laser Speckle Rheology, Conf. Proc. IEEE Eng. Med. Biol. Soc., 2011, pp. 5746-5748.

* cited by examiner

OPTICAL BLOOD-COAGULATION SENSOR

CROSS-REFERENCE TO RELATED APPLICATIONS

This patent applications represents the national stage entry of PCT International Application No. PCT/US2013/076470 filed on Dec. 19, 2013 and claims priority from and benefit of a U.S. Provisional Patent Application No. 61/739,167 filed on Dec. 19, 2012 and titled "Device for Comprehensive Assessment of Blood Coagulation in Real Time". The disclosure of the above-identified provisional application is incorporated herein by reference.

TECHNICAL FIELD

The present invention relates to systems and methods of monitoring of coagulation of blood and, in particular, to a hand-held multi-functional optical blood-coagulation sensor operable at a point-of-care to provide real time simultaneous assessment of at least clotting time, clot formation rate, clot strength, and platelet function.

BACKGROUND

Impaired blood coagulation or coagulopathy is a frequent cause of bleeding and thrombosis following acute trauma and surgery, and is the number one cause of in-hospital preventable death. Multiple factors including the depletion of clotting factors, impaired platelet function and the systemic activation of fibrinolytic pathways contribute to the development of coagulopathy. To manage defective coagulation, blood components are transfused to correct bleeding abnormalities, whereas, anti-coagulant or anti-platelet agents are administered to correct thrombotic conditions. Inadequate therapy can lead to blood loss and affect the performance of organs and acute thrombotic events, while over-transfusion or overuse of anti-thrombotic agents can exacerbate bleeding. In order to achieve optimal outcome and save lives, the early identification of coagulation defects and frequent coagulation monitoring during therapy is essential.

Similarly, millions of patients worldwide receive oral anticoagulant therapy to prevent and treat arterial and venous thromboembolic events, the world's leading cause of mortality. Despite their effectiveness in lowering the risk of acute thrombosis, oral anticoagulants if inadequately monitored, can cause dangerous blood loss and organ failure. Due to numerous drug interactions, underlying comorbidities and the variability of dose response among patents, effective anticoagulation management is often challenging. As a result, patients require frequent laboratory testing of blood coagulation status to ensure accurate and safe anticoagulant dosing. Furthermore, laboratory-based anticoagulation testing is time-consuming and expensive, and provides insufficient information for effective anticoagulant dosing, while placing a huge burden on health-care costs. It is estimated that over 8 million visits are made annually to primary care service providers in the United States for anticoagulant dosing alone, and the service load for anticoagulation management is expected to increase by five-fold over the next decade, imposing an enormous health-care challenge.

Unfortunately, blood tests in the laboratory environment are ineffective in the context of rapidly changing coagulation conditions in critically ill and injured patients. Furthermore, due to the lack of tools available to clinicians for detecting coagulation defects rapidly at the bedside, there are often delays in managing bleeding and thrombosis, increasing the risk of death by 40%. Together, these factors underscore the dire unmet need for routine home-monitoring (at the point-of-care, PoC) of blood-coagulation status to advance the quality of care for patients.

SUMMARY

Embodiments of the present invention provide a hand-held optical thromboelastography system that contains an assembly including a housing unit and a data-processing unit including specifically programmed electronic circuitry. The housing unit contains (i) a base substrate defining a void therein and having a first surface with an aperture providing access to the void; (ii) a superstrate juxtaposed with the first surface over the aperture to form a closed chamber including the void such as to prevent access to said chamber through the aperture; and (iii) a detector disposed to acquire light scattered by a medium within the chamber through the superstrate and to provide a data output representing a cross-polarized speckle pattern generated by the medium. The base substrate is structured to be removably reinsertable into the housing unit, which optionally may include a vibration-isolating platform operable to compensate for a relative movement between the base substrate and the housing unit. The electronic circuitry is programmed to be operable communication with the detector to measure, based on the data output, a time-averaged total reflectance parameter characterizing the medium; to calculate, based on the total reflectance parameter, a mean square displacement associated with optical scatterers of the medium; and to produce an output representing a time-dependent product of a time-dependent effective radius of an optical scatterer of the medium and a viscoelastic modulus of the medium.

Embodiments additionally provide a method for determining a descriptor of coagulation of a stationary blood sample at a point-of-care with an optical thromboelastographer system. The method includes the steps of (a) acquiring light scattered by the stationary blood sample with an optical detector, disposed in a housing removably attachable to a hand-held data-processing unit, where the blood sample is positioned in a chamber formed by a void in a base substrate and an optically-transparent superstrate layered over a surface of the base substrate such as to prevent access to said void through an aperture defined by the void in the surface, and (b) producing a data output representing a cross-polarized speckle pattern produced by the stationary blood sample and compensated for mechanical vibrations of the optical thromboelastographer. The method additionally includes a step of calculating, with a data-processing electronic circuitry contained in the data-processing unit, a plurality of time-dependent parameters associated with the coagulation of the stationary blood sample based on a time-dependent parameter that represents a product of a viscoelastic parameter of the stationary blood sample and a time-dependent radius of an optical scatterer of said blood sample. The plurality of time-dependent parameters includes at least a clotting time, a clot rate, a clot strength, a fibrinogen function, a fibrinolysis function, and a platelet function describing the time-evolution of the blood sample.

Embodiments of the invention additionally provide for an optical thromboelastography system operable at a point-of-case without access to a central server. Such system includes an assembly, containing a housing unit that has (a) a sample cartridge having a chamber in a plane-parallel substrate, (b) an optical train transmitting light that has traversed the chamber, the optical train being devoid of optical power, and (c) a detector disposed to acquire light scattered by a medium within the chamber through the array of optical apertures and to provide a data output representing a cross-polarized speckle pattern generated by the medium. The chamber is optically accessible through a superstrate sealingly overlaying the chamber. The chamber is fluidly accessible through a channel in the substrate. The cartridge is structured to be removably reinsertable into the housing unit.

The thromboelastography system further includes a hand-held data-processing unit with electronic circuitry that is in operable communication with the detector and that is specifically programmed at least (i) to measure, based on the data output, an optical thickness of the medium within the chamber; (ii) to calculate, based on the optical thickness and an autocorrelation function of the cross-polarized speckle pattern, a mean square displacement associated with optical scatterers of the medium; and (iii) to produce an output representing, when the medium includes a stationary sample of blood, a platelet aggregation function and at least first and second parameters including a clotting time, a rate of clot formation, a clot strength, and a fibrinolysis function. The system may additionally include an output device operably cooperated with the electronic circuitry to display a visually-perceivable representation of the output. During the operation of the system, the assembly is optionally removably attached to the output device.

DESCRIPTION OF DRAWINGS

The invention will be more fully understood by referring to the following Detailed Description in conjunction with the Drawings, drawn generally not to scale, of which:

FIG. 1A shows the evolution of clotting time measured from the τ time trace is longer in the hypocoagulable patient relative to normal. FIG. 1B show that fibrinogen levels govern clot stiffness: the blood clot in the hypercoagulable patient with high fibrinogen elicits a higher speckle time constant (τ=80 ms) as compared with normal blood (τ=30 ms).

FIG. 9A: Increasing aggregate radius, a, of polystyrene beads caused by adding $MgCl_2$ salt is detected from MSD changes. FIG. 9B: Detection of a multiple-fold increase in aggregate size with addition of 10 and 5 μM ADP relative to a control sample (with zero ADP).

DETAILED DESCRIPTION

Figures 1A, 1B, 1C:
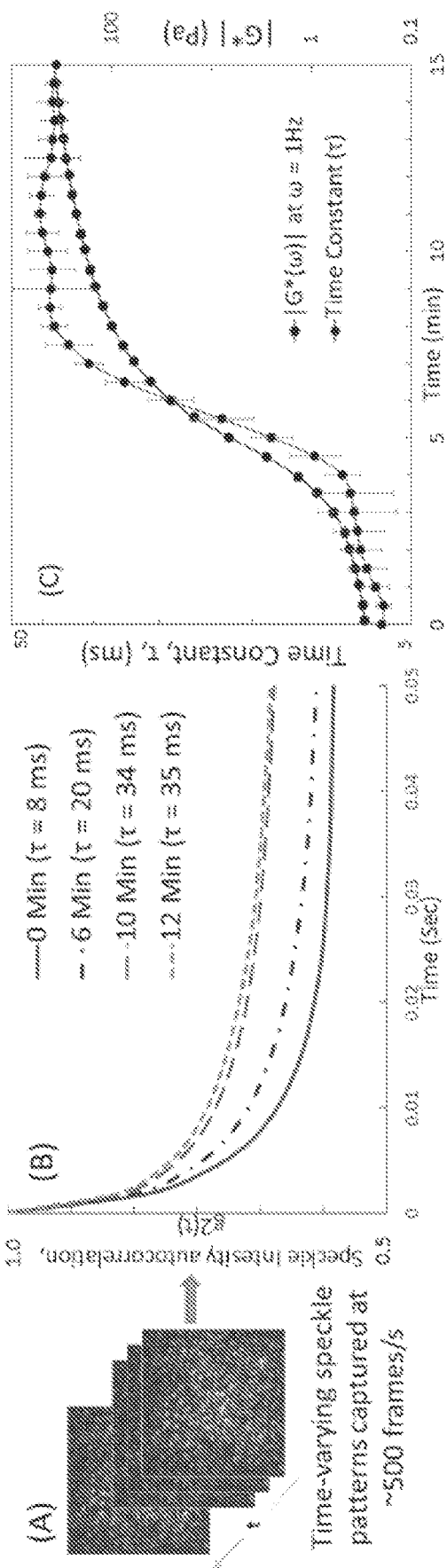
FIGS. 1A, 1B, and 1C show laser speckle time series acquired with an optical detector of a device of the invention are analyzed via 2D cross-correlation to calculate speckle autocorrelation, g2(t), curves during clotting, shown in FIG. 1B. Increasing clot stiffness elicits slower speckle fluctuations corresponding to elevated time constant, τ, that closely corresponds with blood viscoelasticity, G, measured during clotting using a standard ARG2 rheometer, as shown in FIG. 1C.

The present invention addresses the practically unmet needs for routine home-monitoring (at the point-of-care, PoC) of blood-coagulation status by devising a low-cost, optical blood-coagulation sensor operable in conjunction with a smart-phone system, for example, or another handheld data processing and exchange system to quantify blood viscoelasticity, a key indicator of coagulation status, and permit real-time assessment of multiple coagulation parameters. By enabling comprehensive coagulation profiling in a rapid manner, this innovation also improves the safety and effectiveness of oral anticoagulation therapy and lowers the risk of life-threatening bleeding or thrombosis, while reducing the burdensome need for frequent laboratory testing.

To identify the cause of impaired coagulation, numerous laboratory tests are required that evaluate multiple relevant parameters: clotting time, clot formation rate, fibrinogen level, fibrinolysis and platelet function. Unfortunately, given a long turnaround time (about 1 to 4 hrs, in general), these tests often are unreliable in the context of rapidly changing coagulation conditions in trauma and surgical patients. Assessment of coagulation status at the PoC is challenging because current devices provide information limited to clot initiation and fail to identify the underlying cause of impaired coagulation. The only instruments that can facilitate, at this time, the evaluation of the entire coagulation process in real-time are TEG devices (and related rotational TEG or ROTEM devices), which all involve mechanically stirring blood in a cup and measuring viscoelasticity during clotting.

However, TEG and ROTEM devices are large, expensive and difficult to operate, which severely limits their adoption for PoC use. Developing portable TEG and ROTEM sensors for PoC use in the future is likely intractable given the high cost and technical challenges of fabricating and driving miniaturized rotors, ball bearings and cooling elements. Alternatively, surface acoustic wave (SAW) and MEMS based devices are being investigated for viscoelasticity testing. However, due to complexities of precise fabrication and quality assurance, these devices are yet unavailable for clinical use. Other sono-rheometric approaches measure the mechanical response of blood to acoustic perturbation and require complex electronics with adaptive feedback to modulate the acoustic force above the noise threshold but below levels that induce fibrin disruption. Magnetoelastic sensors are recently shown to enable measurement similar to TEG, but the bulky instrumentation needed to emit a magnetic flux and detect resonant frequency shifts, may render them unsuitable for PoC use.

While laser speckle techniques have been investigated to assess coagulation in plasma and whole blood by analyzing speckle contrast changes using a lab-bench setup, the available related art is limited to measuring only clotting time and the capability to quantify clot viscoelasticity and estimate fibrinogen, fibrinolysis and platelet function from speckle fluctuations has not been previously addressed or even mentioned. Moreover, existing to-date instrumentation for speckle rheology utilizes a high-speed camera, bulky electronics and large blood volumes (300 µL), rendering it currently unsuitable for anticoagulation monitoring at home.

Current devices for home use (see Table 1) only provide information limited to clot initiation (measure clotting time) and fail to identify the underlying cause of impaired coagulation and to sufficiently monitor the response of several new anticoagulant agents that act at distinct levels of the coagulation cascade.

TABLE 1

State-of-the-art blood coagulation sensors

| Device and mode of operation | Primary care/ home use | Parameters measured | Limitations |
| --- | --- | --- | --- |
| Electrical impedance (CoaguChek ®) | ✓ | clotting time | Information limited to clotting time Cannot assess fibrinogen, platelet function, clot strength or fibrinolysis |
| Optical (CoagDx ®) | ✓ | clotting time | Cannot to detect underlying coagulation defect |
| Microelectromechanical systems (MEMS) (CoagMax ®) | ✓ | clotting time | Complex MEMS device fabrication, testing and quality assurance Only measures clotting time (as above) No clinical validation studies yet reported Not yet available for clinical use |
| Light transmission aggregometry (VerifyNow ®) | X | platelet function | Limited to platelet aggregation measurement Lacks capability to measure clotting time and other coagulation parameters |
| Whole blood viscoelasticity testing: Mechanical Thromboelastography (TEG ®) | X | clotting time, fibrin formation, platelet function, clot strength, fibrinolysis | Large size, needs experienced operators, large blood volume, high cost (>$80,000) Not portable, difficult to transport Requires pipetting and mixing blood with activators Not approved for home use |

Warfarin, a commonly prescribed vitamin K antagonist broadly inhibits multiple clotting factors. Due to the elevated bleeding risk associated with Warfarin use, new drugs with improved safety profiles are recently approved that target specific clotting factors. Foremost among there are Factor Xa and direct thrombin inhibitors (DTI) that inhibit thrombin activation and the downstream conversion of fibrinogen to fibrin, as well as antiplatelet agents that reduce platelet aggregation, a critical process in clot initiation. Therefore, depending on the type of agent administered, besides clotting time, additional coagulation parameters require monitoring to assess thrombin function, fibrin cross-linking or platelet aggregation. Unfortunately, due the absence of tools for timely and comprehensive anticoagulation monitoring, many patients are exposed to an elevated risk of life-threatening bleeding or thrombosis caused by unsafe or inadequate anticoagulant dosing.

These challenges are addressed by developing a low cost multifunctional optical coagulation sensor (or OCS, or an OTEG device) based on an optical module interfaced with an external data-processing unit (optionally cooperated or integrated with a smart phone), which optical module incorporates a laser source and an optical detector (for example, a photodiode array) to collect light intensity fluctuations acquired from a single drop of blood.

Embodiments of the optical coagulation sensor and method of blood-monitoring with such sensor is based on a novel laser speckle rheology (LSR) approach. Laser speckle, formed by the interference of laser light scattered from tissue, is dynamically modulated by the endogenous Brownian motion of light scattering particles, governed by the viscoelastic properties of tissue. During the process of blood coagulation, the increasing stiffness of the fibrin clot restricts the motion of light scatterers, eliciting a slower rate of speckle intensity fluctuations compared to whole blood.

Furthermore, while the time scale, $\tau$, of speckle intensity fluctuations is intimately related with blood viscoelasticity and is acutely indicative of blood coagulation status, the metric that defines the viscoelastic properties of clotting blood is the viscoelastic modulus, G. By measuring changes in the viscoelastic modulus of whole blood over time during clot initiation, fibrin crosslinking, clot stabilization and fibrinolysis (i.e., by providing the optical thromboelastographic measurements, or OTEG measurements), an embodiment of the invention generates an output containing complete information of the entire coagulation process as it evolves. As a result, using a drop of blood obtained by a fingerstick draw, an implementation of the optical coagulation sensor (interchangeably referred to herein as optical thromboelastographer) according to the idea of the invention enables the unparalleled opportunity to assess a multiplicity of coagulation parameters at the same time, for the robust home-monitoring.

Figure 2A:
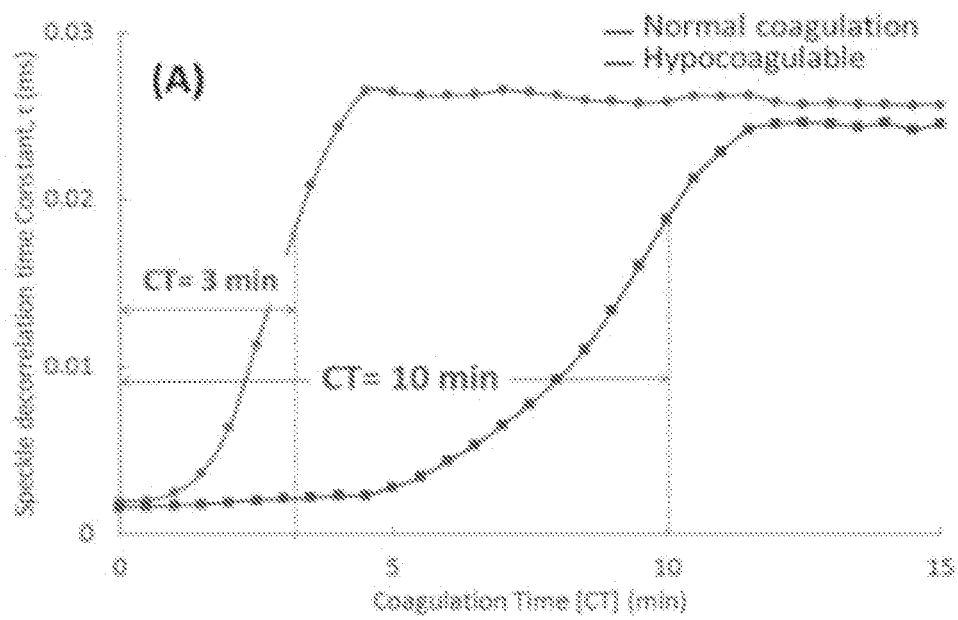
FIGS. 2A, 2B illustrates plots (time traces) of τ represents changing clot viscoelasticity to detect coagulation defects.
Figure 2B:
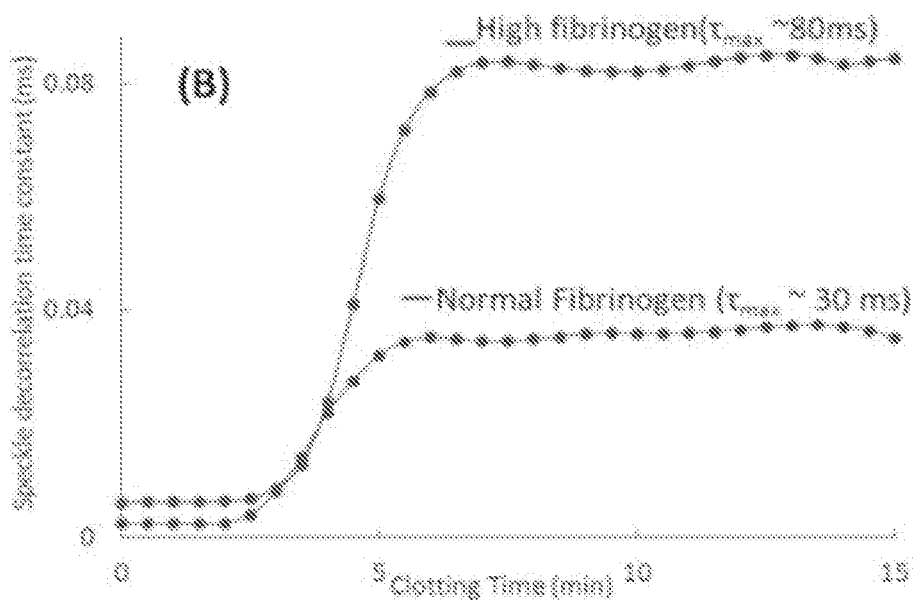

FIGS. 1A, 1B, 1C provide illustration to the concept. Laser speckle time series in FIG. 1A are analyzed via 2D cross-correlation to calculate speckle autocorrelation, $g_2(t)$, curves during clotting, FIG. 1B. Increasing clot stiffness elicits slower speckle fluctuations corresponding to elevated time constant, $\tau$, that closely corresponds with blood viscoelasticity, G, measured during clotting using a standard ARG2 rheometer, FIG. 1C. FIG. 2 illustrates the significance of OSC parameters. Whole blood viscoelasticity trace permits assessment of the entire coagulation process. Relevant parameters derived from the trace provide information on reaction time for prothrombin activation (R), clotting time (R+K), rate of fibrin cross-linking (a), clot stiffness (MA) related to thrombin function, and clot stability (% LY).

Unlike mechanical and acoustic devices, an OCS does not require large moving parts, bulky electronics or complex MEMS assemblies to manipulate or perturb the sample. The OCS quantifies multiple relevant coagulation parameters including clotting time, clot rate, fibrinogen, fibrinolysis and platelet function within <½ the time and at <$\frac{1}{100}^{th}$ the cost of the TEG modality. Because the LSR-based OCS modality measures optical phase shifts of acquired light caused by nanometer-scale particle motion, it is exquisitely sensitive to minute changes in clot viscoelasticity, permitting detection of early micro-clots within <5 minutes using a single drop of blood.

In addition to clot viscoelasticity, platelet function that defines the ability of platelets to aggregate and initiate clotting, is a highly relevant parameter to inform transfusion needs or monitor anti-platelet therapy. According to the idea of the invention, present embodiment implement the evaluation of aggregation of blood platelets from the detected speckle fluctuations. Thus, in a single hand-held module, the device of the invention enables the unparalleled capability to rapidly quantify multiple coagulation parameters: clotting time, clot formation rate, clot strength (related to fibrinogen), fibrinolysis and platelet function, at the bedside.

Faivre M. et al., in "Coagulation dynamics of a blood sample by multiple scattering analysis", (J. Biomed Opt. 2011; 16:057001) have reported the feasibility of measuring clotting time in whole blood by analyzing speckle contrast variations. However, the capability to quantify clot viscoelasticity and estimate fibrinogen, fibrinolysis and platelet aggregation proposed here has not been addressed yet. An embodiment of the present invention is structured to implement laser-speckle data processing schemes to estimate blood optical properties, calculate Brownian displacements of endogenous light scatterers, and plot blood viscoelasticity during clotting in real-time. The capability for rapid platelet function testing is implemented by measuring aggregate growth from temporal speckle fluctuations via the same device. Data processing, reporting and the GUI are completely automated to mitigate human errors. Clot viscoelasticity and platelet aggregation measurements is recorded according to a predetermined schedule (for example, every 30 s) to permit reporting of relevant coagulation parameters as they evolve in real-time.

Embodiments of the Device and Data Acquisition and Processing Algorithm

Example 1

An embodiment 300 of the optical thromboelastographer (or OCS) of the invention are schematically illustrated in FIGS. 3A, 3B, 3C. An embodiment includes an assembly containing a housing unit 304 that hosts a re-insertable cartridge 308 having a dedicated container for a medium scattering light incident thereon from the coherent light source 312 (a laser diode, for example) that gives rise to a laser-speckle detected with an optical detector 316. A major limitation in conventional TEG measurements is the requirement for cumbersome blood sample preparation that involves pipetting and mixing precise volumes of blood, coagulation activators and reagents prior to testing. As a result TEG is often relegated to a central laboratory setting causing delays in accessing test results. To address these limitations of the existing TEG modality, in one implementation the cartridge 308 will include a small chamber (for example, several millimeters in diameter) constructed within a 1-2 mm thick, blood-compatible silicone base, optionally sandwiched between two optically clear polycarbonate films (with thicknesses of a part of millimeter, for example 0.15 mm). To operate the device, a few drops of whole blood are placed within the cartridge (V<100 μL) secured in place within the cartridge slot. To optionally permit direct comparison of OTEG coagulation parameters with TEG, standard coagulation activators and agonists (e.g., kaolin, ADP) are titrated, preloaded within the cartridges and provided for use. Accordingly, the cartridge 308 may includes a base substrate 320 defining a void and having a first surface with an aperture providing access to such void. The cartridge 308 may further include a superstrate 324 juxtaposed with the first surface over the aperture to form a closed chamber including the void such as to prevent access to said chamber through the aperture. Since that the laser speckle information, from which the OCS device is determining the relevant blood-coagulation parameters, is susceptible to external vibrations, an embodiment of the device optionally incorporates a vibration-isolating platform (not shown) operable to compensate for a relative movement between the base substrate and the housing unit. Time-averaging and Fourier domain filtering of $g_2(t)$ curves can be optionally implemented to remove the influence of residual instabilities. The embodiment 300 further includes a hand-held data-processing unit 330 that includes programmable electronic circuitry in operable communication with the detector 316. The housing 304 and the data-processing unit 330 are removably and operably connected to one another through, for example, a C-mount.

The frequency-dependent viscoelastic modulus, $G(\omega)$, traditionally measured using a mechanical rheometer (TEG), can also be quantified optically by evaluating the mean-square displacement (MSD) of light scattering particles from speckle intensities (at the optical detector 316) that fluctuate at frequency $\omega$ and by using a continuum approximation of light diffusion to describe the MSD-g2(t) relationship. The modulus, $G(\omega)$, can be then estimated from the MSD via the generalized Stokes-Einstein relation (GSER). The challenge in quantifying the viscoelastic properties of clotting blood is that, temporal speckle fluctuations are governed not only by the MSD of light-scattering particles, but also by optical absorption and scattering variations (defined by coefficients, $\mu_a$ and $\mu'_s$ of the blood) during the coagulation process. To take optical absorption and scattering variations into account, an embodiment of the algorithm of the invention, schematically shown in a flow-chart of FIG. 4, includes a step of estimation of optical properties from time-averaged speckle images [shown in boxes 1,2] acquired with the detector 316; the implementation of a simplified solution that corrects for these optical factors and estimates the MSD from the measured $g_2(t)$ [as shown in boxes 1,2,3]; the utilization of the GSER to quantify $G(\omega)$ [box 4a], and quantify platelet aggregate size, a, via the Stokes Einstein relation (SER) [box 4b].

Figure 4A:
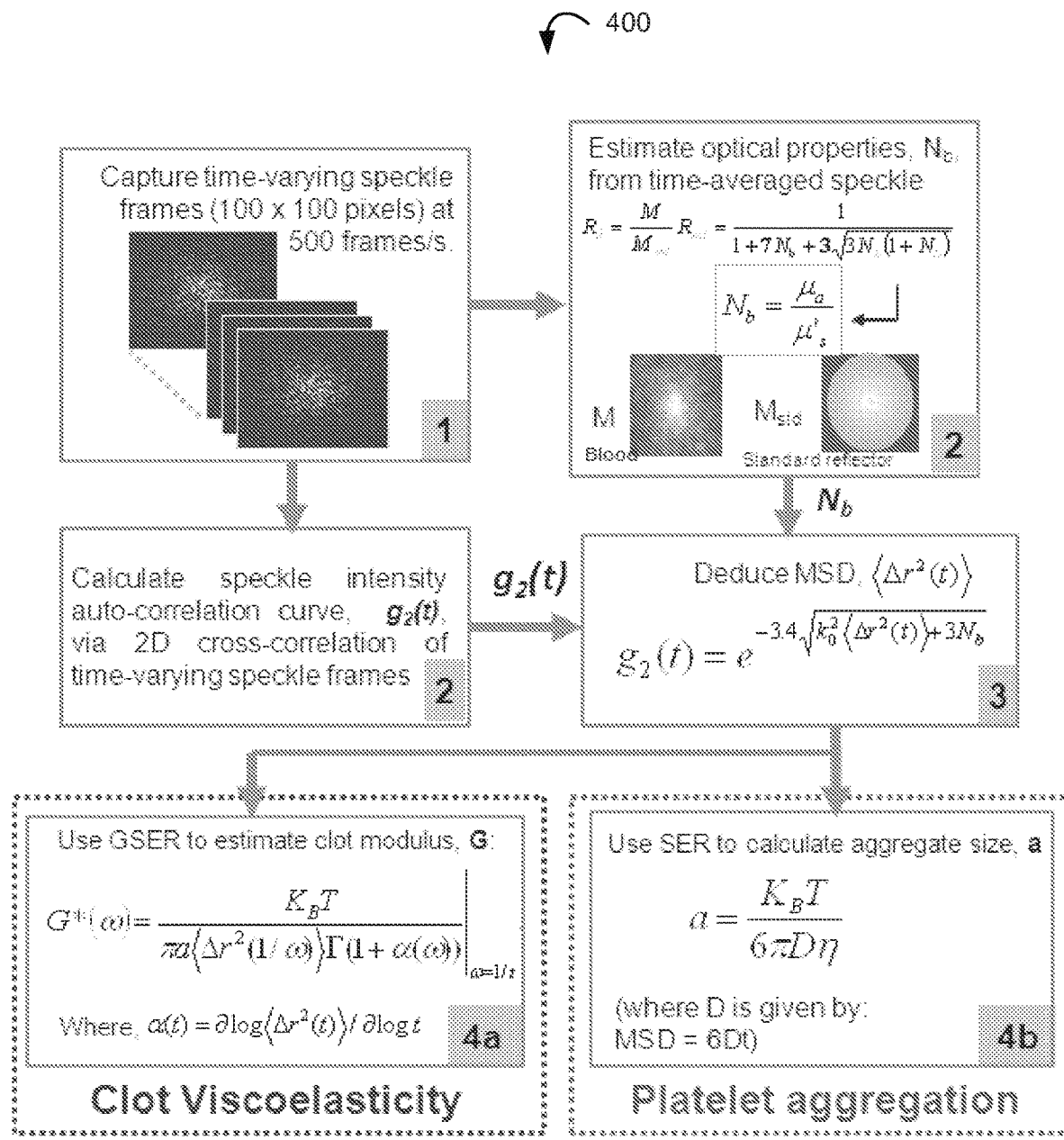
FIG. 4A is a flow-chart for an OTEG algorithm for real-time laser-speckle data processing: Box 1: Time-varying series of speckle frames is captured at a high frame rate. Box 2: Speckle images are processed in two ways: Normalized 2D cross-correlation of speckle time series yields the speckle autocorrelation, $g_2(t)$ curve. Time-averaging of speckle frames yields reflectance $R_d$ which is compared with a standard to estimate the $\mu_a/\mu'_s$ ratio. Box 3: A simplified closed form equation is used to estimate MSD from the measured $g_2(t)$ and $\mu_a/\mu'_s$. Box 4: (a) The MSD is substituted in the Generalized Stokes-Einstein Relation (GSER) to yield the viscoelastic modulus of blood. (b) The effective scatter radius, a, is measured from the Stokes-Einstein relation (SER) to yield aggregate size in unclotted blood spiked with a platelet agonist.

A flow-chart of FIG. 4A illustrates an embodiment 400 of the algorithm of real-time laser-speckle data processing, which is discussed below.

Estimating Blood Optical Properties:

In reference to the flow-chart of FIG. 4A, the robust calculation of MSD from the speckle autocorrelation curve, $g_2(t)$, also requires information about blood optical properties [box 3]. According to an embodiment of the invention, the speckle pattern time series acquired with the detector 316 of FIG. 3A from the light-scattering medium contained in the chamber of the cartridge 308 is processed in parallel to compute both the $g_2(t)$ curve from time-resolved intensity fluctuations, and optical properties from time-averaged speckle intensities [boxes 2]. Since the MSD is influenced by the ratio of optical absorption to scattering ($\mu_a/\mu'_s$), independent estimates of $\mu_a$ and $\mu'_s$ may simply not be needed. Optionally, the $\mu_a/\mu'_s$ ratio can be simply calculated from the total reflectance, $R_d$ as $$R_d = \frac{1}{1 + (2K+1)\frac{\mu_a}{\mu'_s} + \left(1 + \frac{2K}{3}\right)\sqrt{3\frac{\mu_a}{\mu'_s}\left(1 + \frac{\mu_a}{\mu'_s}\right)}} \quad (1)$$

where $K=(1+r_d)/(1-r_d)$, $r_d=-1.44\ n_{rel}^{-2}+0.71\ n_{rel}^{-1}+0.668+0.0636\ n_{rel}$, and $n_{rel}=n_b/n_v$ is the relative refractive index of the blood-air interface. Given the ratio of blood-air refractive indices, K of about 3 is derived. To estimate the total reflectance $R_d$, a one-time calibration of the OCS device of the invention is carried out using a reflectance standard (such as, for example, Spectralon®, 0.55"×1.5" with a reflectance factor of $R_{std}$=50%) to record the mean pixel value, $M_{std}$, via temporal and spatial averaging of speckle frames. Since all measurements are relative, it is not necessary to convert pixel values to absolute intensity. Instead, when evaluating blood specimens, the mean pixel value, M, is similarly evaluated via spatio-temporal speckle averaging, and $R_d$ is directly calculated as: $R_d=M/M_{std}\times R_{std}$. The ratio $\mu_a/\mu'_s$ is computed from Eq. (1) using a simple change of variables and simple algebraic manipulations. This approach was verified in glycerol mixtures by tuning concentrations of carbon and $TiO_2$ microspheres suspended in the glycerol, to span a wide range of $\mu_a/\mu'_s$ values (0.022-0.45). So experimentally evaluated $\mu_a/\mu'_s$ closely correlated with values obtained in reliance on Mie theory (R=0.92, p<0.001). The same strategy was tested in human blood with light at 690 nm ($\mu'_s$~1.1 $mm^{-1}$, $\mu_a$~0.15 $mm^{-1}$) and confirmed that $\mu_a/\mu'_s$~0.133 measured as above closely matched values disclosed in related art ($\mu_a/\mu'_s$~0.136). The algebraic process for deriving $\mu_a/\mu'_s$ from $R_d$ via Eq. (1) follows the following expression:

$$u = \frac{-3R_d - \sqrt{R_d^2 + 6.667R_d + 1.33}}{0.667(R_d - 1)}, \quad \frac{\mu_a}{\mu'_s} = \frac{1}{u^2/3 - 1} \quad (2)$$

Estimating Clot Viscoelasticity:

To calculate the MSD, the $g_2(t)$ curves are measured via the normalized cross-correlation analysis of the first speckle frame with the subsequent time series (box 2). The estimated $\mu_a/\mu'_s$ ratio calculated as above, is replaced in the equation of box 3, and resultant the MSD is extracted. The viscoelastic modulus $G(\omega)$ is then calculated via the GSER using previously established mathematical formalisms (box 4a). For example, the logarithmic slope, $\alpha(t)$, of the MSD is evaluated, and the algebraically approximated Fourier transform of the MSD is obtained from $\alpha(t)$ and substituted in the GSER to quantify $G(\omega)$.

Figure 5:
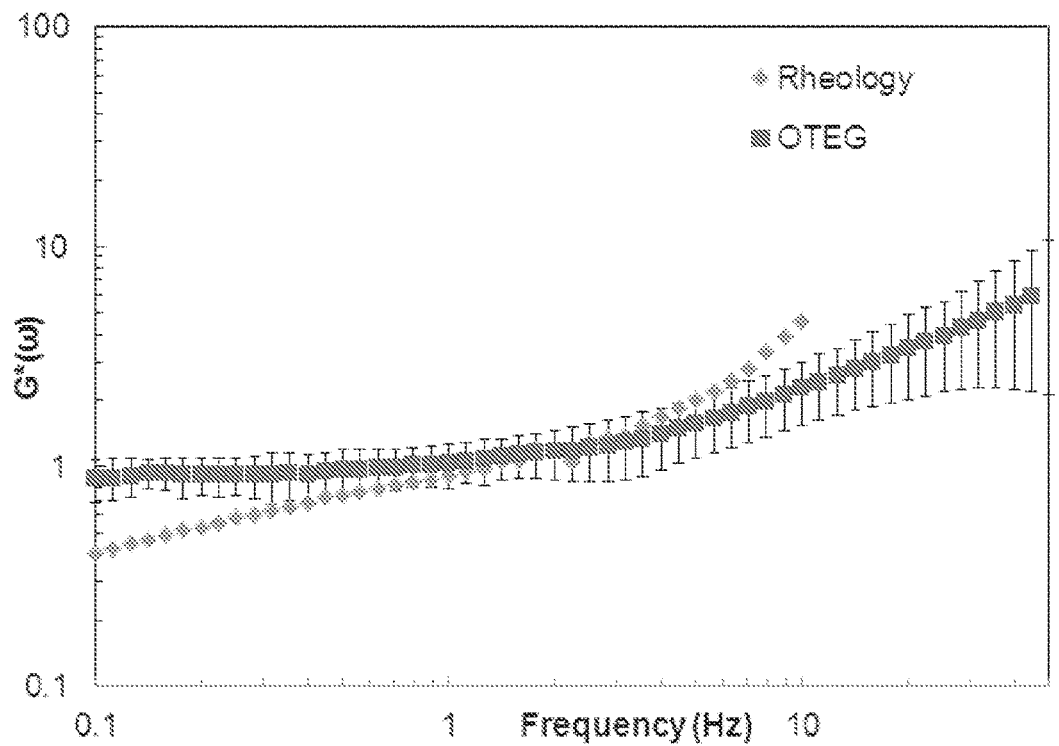
FIG. 5 shows a comparison of a plot representing the frequency-dependent viscoelastic modulus of a human blood sample determined with an OTEG embodiment of the invention with that determined with the use of conventional rheometric measurement.
Figure 6:
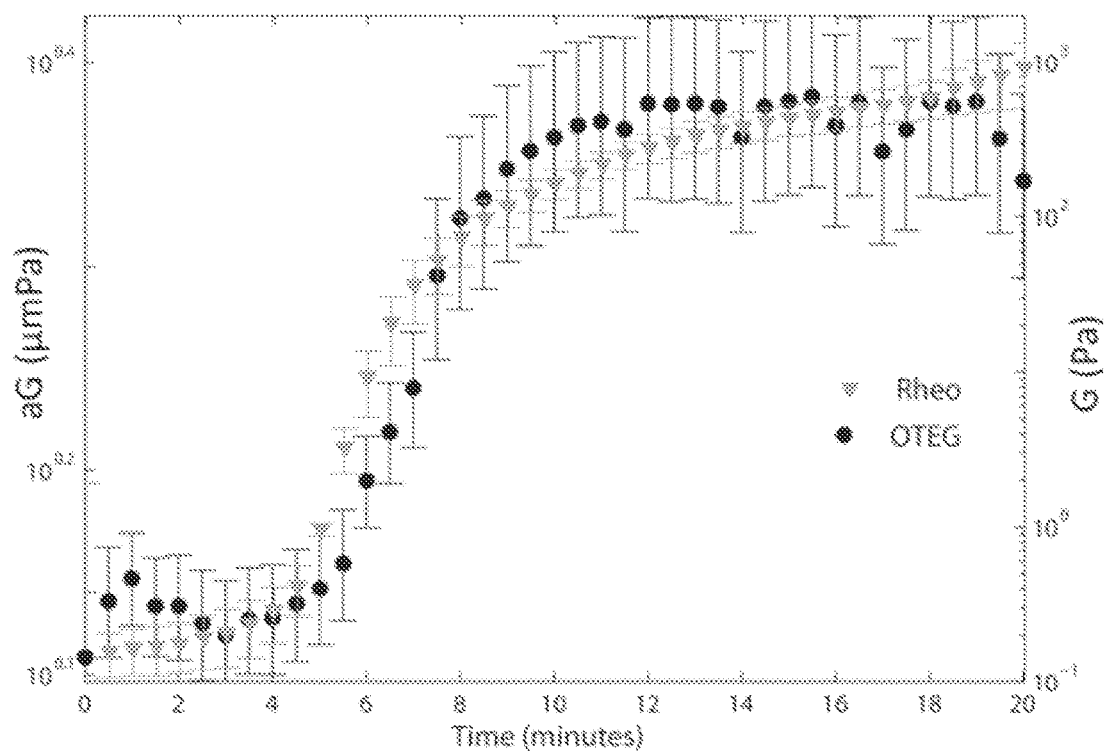
FIG. 6 shows a comparison of a plot representing the time-dependent product of a modulus of viscoelastic modulus (determined at a chosen single frequency) of a human blood sample scaled by a radius of optical scatterer with time-evolution of viscoelastic modulus determined with the use of conventional rheometric measurement.

The plots of FIG. 5 were drawn by applying the above-described processing scheme of the invention to quantify $G(\omega)$ of human blood samples; the results closely mirror the results obtained with conventional rheometry. To quantify the absolute value of $G(\omega)$ during clotting, an estimate of the effective particle radius, a, undergoing Brownian motion is needed. Since the parameters, a and $G(\omega)$, are both altered due to platelet aggregation and fibrin clot formation, the accurate estimation of particle size conventionally involves complex and bulky instrumentation that is simply not structurally compatible with the hand-held design of the OCS device of the invention. To obviate this problem, in an embodiment of the invention a different quantity—the quantity $G=aG(\omega')$, which represents the viscoelastic modulus scaled by a scattering particle diameter a—is measured at a single frequency, $\omega=\omega'$. As shown in FIG. 6, it was experimentally confirmed that relative changes in clot viscoelasticity defined by a time-dependent product aG closely follow the evolution of the viscoelastic modulus measured with conventional mechanical rheometry. Based on the results of one specific implementation, the G values derived from the measurement at 5 Hz provided the optimal correlation with the results of both mechanical rheometry (FIG. 6) and TEG (the latter comparison presented and discussed in reference to FIGS. 8A, 8B below).

Figure 7:
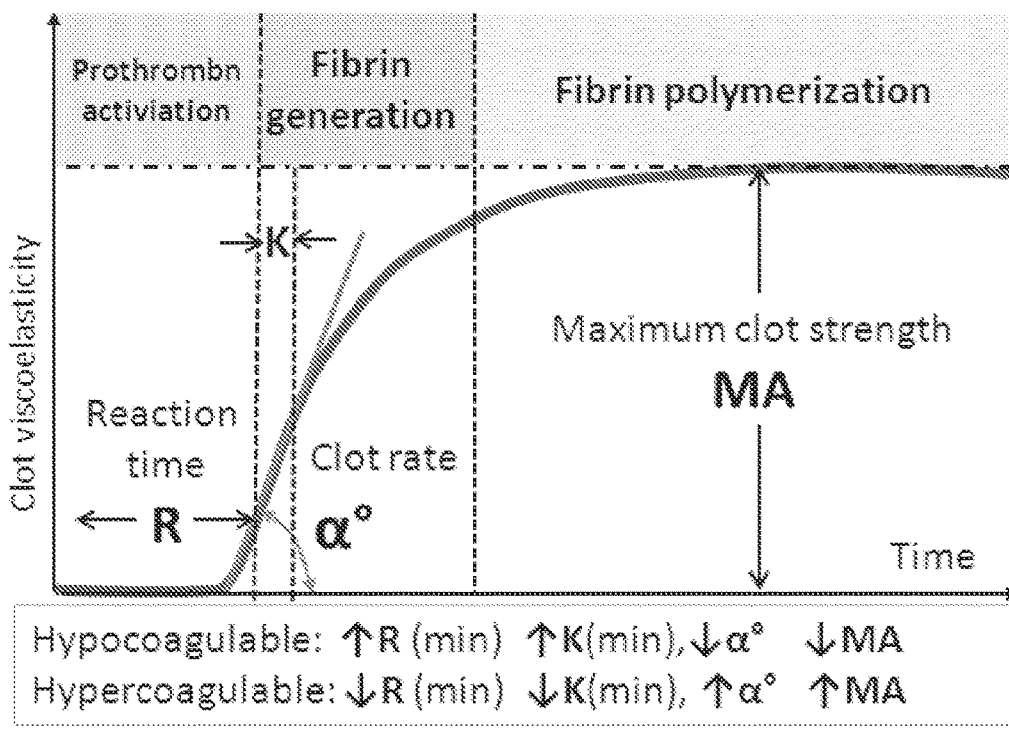
FIG. 7 illustrates the significance of OTEG parameters: Whole blood viscoelasticity trace permits assessment of the entire coagulation process. Relevant parameters derived from the trace provide information on reaction time for thrombin generation (R), clotting time (R+K), rate of fibrin cross-linking (a), clot stiffness (MA) proportional to fibrinogen levels, and clot stability (% LY) to detect hyperfibrinolysis.

The recordation of an OCS trace representing the blood-coagulation cascade with a device of the invention permits assessment of relevant coagulation parameters to monitor a variety of anticoagulant agents that act at specific levels of the coagulation cascade, FIG. 7. For instance, long R times may indicate inhibition of prothrombin activation by Factor Xa inhibitors, and low a may indicate increased thrombin inhibition that mediates the conversion of fibrinogen to a fibrin clot. Since the extent of fibrin cross-linking is directly related to clot strength, MA values may be closely related with DTI dose.

Typically, the blood coagulation is a slow process evolving over at least several minutes (for example, 10 to 15 min). Accordingly, a measurement interval of about 30 seconds or shorter permits ample temporal sampling of the entire coagulation cascade in real-time.

Figure 8A:
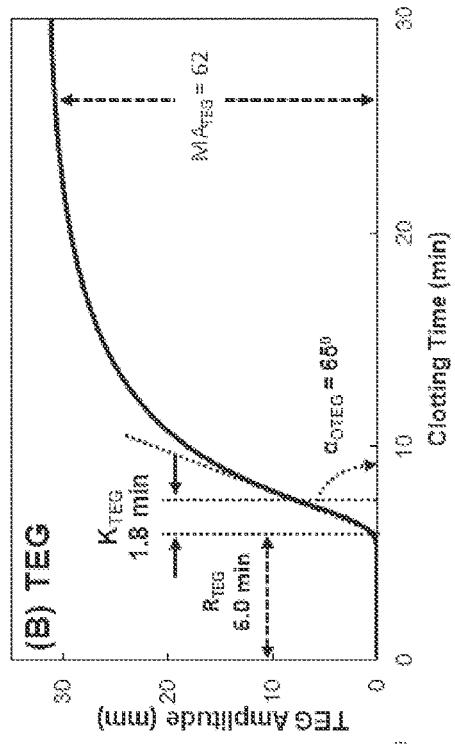
FIGS. 8A, 8B show plots illustrating preliminary data obtained using existing bench-top implementation of the OTEG device (FIG. 8A) versus standard TEG curves (FIG. 8B) measured in a normal human blood sample.
Figure 8B:
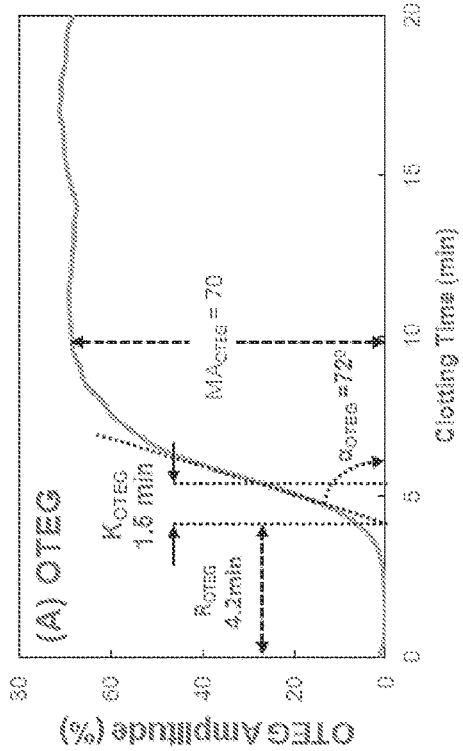

Deriving Blood Coagulation Parameters from the OTEG Viscoelasticity Trace:

To permit direct comparison between the results obtained with the use of an embodiment of the invention and the results obtained with the conventional TEG modality, an identical approach is applied to plot the change in G relative to whole blood (at time=0) and to similarly obtain an OTEG amplitude curve that describes the time-course of blood coagulation, as shown in FIGS. 8A, 8B. Close correspondence is observed between the two viscoelasticity time traces. Due to its superior sensitivity to small changes in viscoelasticity, the OTEG results are delivered about twice as fast as TEG, as seen by shorter R times, and the total time to MA is about half of that in TEG (10 min in OTEG versus 20 min in TEG). In reference to FIGS. 7 and 8A, the following methods were used to calculate coagulation metrics from the OTEG plots: The modulus, G(t), was calculated as discussed above and plotted as a function of time, t. The derivative of the data expressed by G plot was calculated (dG/dt) and the time required to reach the maximum value of dG/dt was reported as clotting time (R+K). Alternatively, a tangent line was drawn to the rising edge of the G(t) plot, and the value corresponding to time at which the tangent intersected the time axis was reported as R, while the time required to reach the maximum value of G (a knee of the G(t) curve) was reported as K. The MA was reported as the average plateau amplitude of the G(t) curve.

By implementing methods that have been established and FDA-approved for TEG analysis, the following coagulation parameters are extracted from the viscoelasticity curve obtained from the OTEG-based measurements: the reaction time ($R_{OTEG}$), the clot formation time ($K_{OTEG}$), the rate of clot formation ($\alpha_{OTEG}$), the maximum OTEG amplitude ($MA_{OTEG}$), and the extent of fibrinolysis (% $LY_{OTEG}$).

Assessment of Platelet Aggregation from Laser Speckle Fluctuations.

By providing additional capability to evaluate platelet aggregation, the proposed OCS device and methodology would aid in monitoring antiplatelet therapy in patients being treated for cardiovascular disease. Platelet aggregation plays a key role in clot initiation and supports many downstream reactions in the coagulation cascade. The current standard for platelet assessment is light transmission aggregometry (LTA) which evaluates platelet aggregation by measuring changes in turbidity of platelet rich plasma caused by addition of the platelet agonist composition such as, for example, adenosine diphosphate (ADP), epinephrine, arachidonic acid, thrombin, or collagen. An LTA-based PoC device is currently available for clinical use to evaluate platelet aggregation, but it is incapable of assessing other coagulation parameters enabled in real time by the OTEG device of the present invention (see Table 1). While the feasibility of detecting platelet aggregation from speckle size changes has been previously reported, the reported method required plasma by centrifuging blood and is not conducive to PoC use. To enable platelet function assessment via the OTEG device) or, OCS device) of the invention, the platelet aggregation is quantified in whole blood. To this end, citrated whole blood is transferred into an OTEG cartridge 308, preloaded with ADP solution and time-varying speckle patterns are captured according to the algorithm described above in reference to FIG. 4. During the data acquisition, the platelet agonist composition (such as ADP) selectively triggers conformational changes in platelets and induces platelet aggregation with minimal influence on RBCs. Thus, an increase in the average scattering particle radius can be predominantly attributed to platelet aggregation. Since the blood is citrated ($Ca^{++}$ ions are absent), the fibrin cascade is not initiated and blood viscosity, η, remains largely unchanged at η=4 cP (at about 37° C.). Compared to small isolated platelets (diameter of about 3 μm), the platelet-agonist-induced activation causes large platelet aggregates to appear that experience a shorter range of diffusive motion and induce slower speckle fluctuations. To estimate the rate and extent of platelet aggregation, speckle frames are processed and MSD values are calculated (according to steps shown in [boxes1-3] of FIG. 4). The flow-chart of FIG. 4A presents an expression through which $g_2(t)$ relates to MSD, when speckle acquisition is conducted in backscattering geometry. In comparison, when speckle patterns are acquired in transmission geometry, $g_2(t)$ is expressed in terms of MSD, as shown in flow-chart of FIG. 4B. The calculated MSD is then automatically fitted to a simple linear model of MSD=6Dt, or equivalently the slope of MSD is calculated, at early times to estimate the diffusion coefficient, D, of scattering particles. Alternatively, it is possible to substitute 6Dt in the flowcharts of FIGS. 4A and 4B, and directly fit the $g_2(t)$ curves, to a parametric exponential function, in which D is incorporated as a fitting parameter. For instance, in back-scattering geometry, the experimentally evaluated $g_2(t)$ curve can be fitted to the following model:

$$g_2(t) = e^{-2\gamma\sqrt{6k_0^2 n^2 Dt + \frac{3\mu_a}{\mu_s'}}} \quad (3)$$

For the transmission geometry, the parametric model is given by:

$$g_2(t) = \left( \frac{3L/l_B^* + 4}{5} \frac{\sinh\left(\sqrt{6k_0^2 n^2 Dt}\right) + 2/3\sqrt{6k_0^2 n^2 Dt}\cosh\left(\sqrt{6k_0^2 n^2 Dt}\right)}{\left(1 + \frac{8}{3}k_0^2 n^2 Dt\right)\sinh\left(\frac{L}{l_B^*}\sqrt{6k_0^2 n^2 Dt}\right) + 4/3\sqrt{6k_0^2 n^2 Dt}\cosh\left(\frac{L}{l_B^*}\sqrt{6k_0^2 n^2 Dt}\right)} \right)^2 \quad (4)$$

$$\approx \left( \frac{(L/l^* + 4/3)\sqrt{6k_0^2 n^2 Dt}}{\sinh\left((L/l^* + 4/3)\sqrt{6k_0^2 n^2 Dt}\right)} \right)^2$$

Figure 9A:
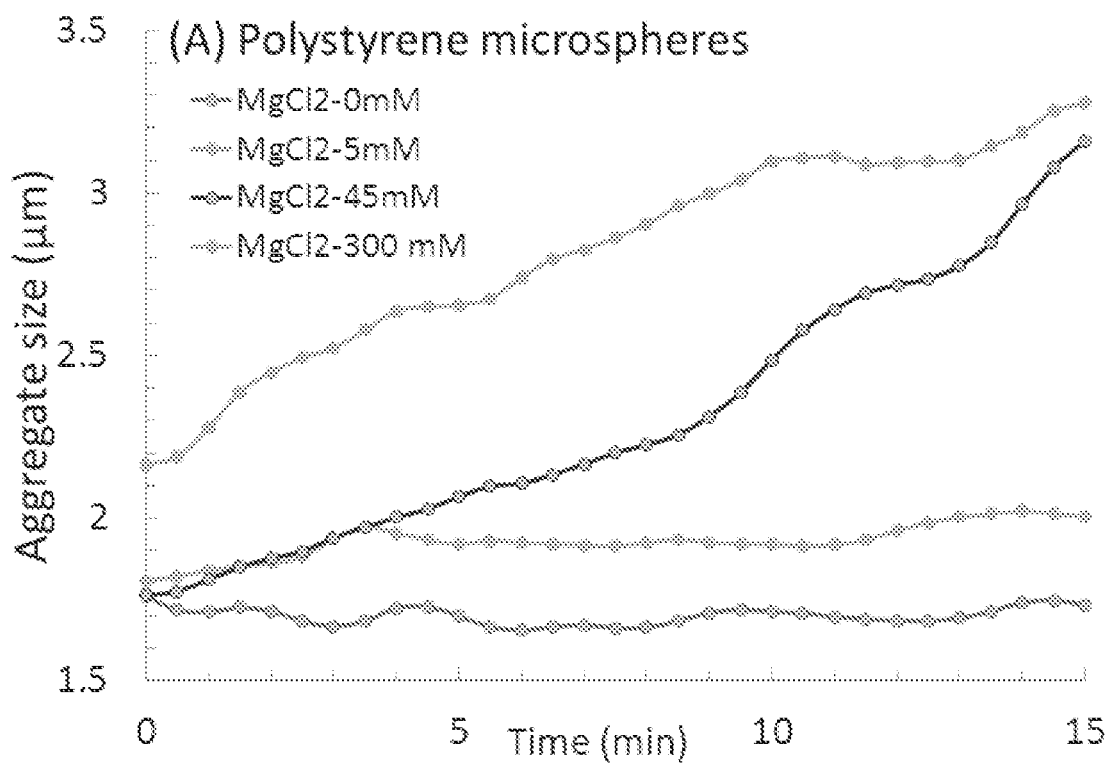
FIGS. 9A, 9B illustrate the results of determination of platelet aggregation from the detected speckle intensity fluctuations.
Figure 9B:
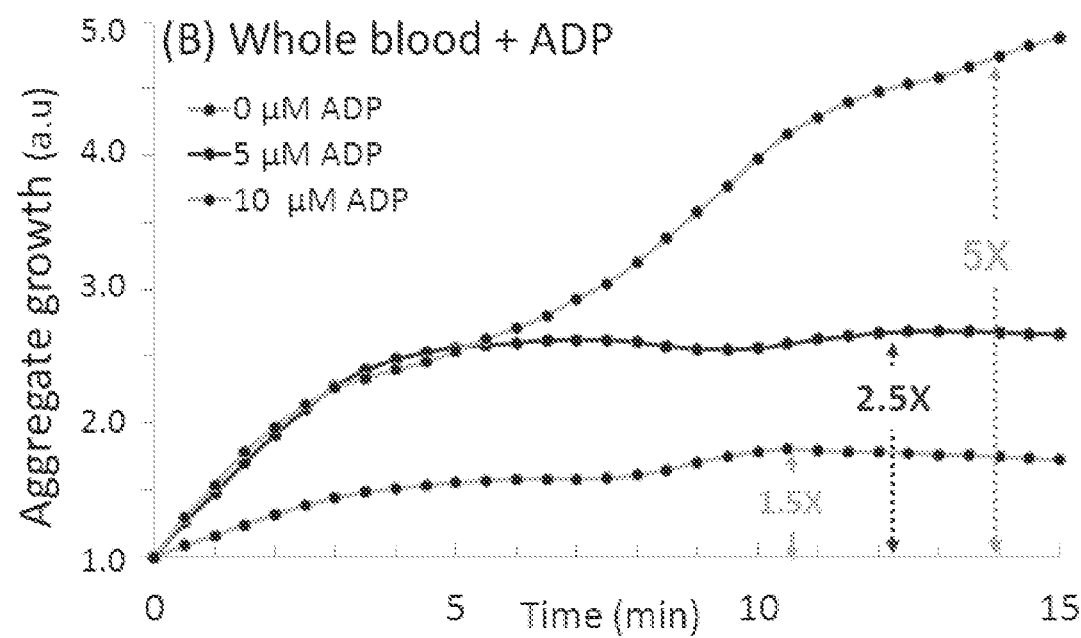

The effective particle radius, a, is then obtained from the Stokes-Einstein relation (SER) (FIG. 4A, box 4b). In other words, $a=K_b T/(6\pi \eta D)$, where $K_b=1.3806488\times 10^{-23}$ is the Boltzman constant, T=312 is the blood temperature (degrees Kelvin), $\eta$=4 centipoises is the viscosity of the blood, and D is the diffusion coefficient of the scattering particles. The aggregate growth from the baseline at time t=0 is plotted, and the maximum extent of platelet aggregation (PA) is estimated at a predetermined time (for example, at 10 minutes) to quantify platelet function, as shown in FIGS. 9A and 9B. More specifically, the rate of aggregation is estimated by drawing a tangent line to the aggregate-size profile, i.e. a(t) at the launch of aggregation process, where the slope is steep. The value of the slope is a direct indicator of the rate of the biochemical processes of platelet aggregation, such as the release of dense granules, and the additional release of ADP and thromboxane by platelets, which leads to the activation and the aggregation of additional platelets. Depending on the concentration of the agonist, a second wave of aggregation may be observed, which is identified by an intermediate plateau of the a(t), followed by another steep growth of the curve. The a(t) curve eventually flattens, at a predetermined time, $t_p$. The $a(t_p)$ is then reported as the maximum platelet aggregation, PA. If PA is with a predetermined diagnostic normal, the platelet function within the test blood sample may be declared normal. Otherwise, the platelet aggregation rate and maximum value when outside the range, may be reported as abnormal.

Preliminary assessment of platelet aggregation using the OTEG modality is shown for human whole blood. An embodiment of the device detected a small increase in aggregate size in the control sample (no ADP) is likely caused by RBC sedimentation.

Platelet aggregation also effectively modifies the blood optical properties, and particularly the reduced scattering coefficient, $\mu_s'$. The scattering coefficient is given by $\mu_s = \rho \sigma$ where $\rho$ is the number density of scattering particles and $\sigma$ is the scattering cross section. For poly-disperse suspensions, such as blood, $\mu_s$ may be expressed by the following expansion, in which summation is over the scattering particles of discrete sizes, which may include RBCs, platelets, WBC, and blood macromolecules of dimensions larger than a few nano-meter that may effective scatter the light at the given source wavelength. Thus, $\mu_s = \Sigma_{i-1}{}^n \rho_i \sigma_i$, where $\rho_i$ is the number density of the $i^{th}$ set of scattering particles with the identical scattering cross section of $\sigma_1$. Suppose that the number density of platelets is $\rho_j$ (which is typically 1.5-4× $10^5$ per mm$^3$ in the normal blood). In addition, the scattering cross section of platelets is directly proportional to their geometric cross section (dia. 2-3 μm). When platelets aggregate, the scattering cross section of aggregates, $\sigma_j'$, grows larger than isolated platelets; however, the number density of the isolated platelet clumps, $\rho_j'$, reduces as now there are less isolated scattering centers. Thus, in effect, $\rho_j' \sigma_j' < \rho_j \sigma_j$ and consequently, the overall scattering coefficient decreases by platelet aggregation. In addition light scattering by aggregates of larger scattering cross section tends to be more forwardly directed and less isotropic. As a result, the total anisotropy factor of of the blood, g, is increased (i.e. backward to forward scattering ratio, g=-1 for totally backward scattering, g=1 for primarily forward scattering, and g=0 for isotropic scattering, for blood typically g>0.95) and the reduced scattering coefficient $\mu_s' = \mu_s(1-g)$ reduces, significantly.

Since platelet aggregation reduces the $\mu_s'$, both diffuse reflectance profile, DRP, (denoted as R($\rho$), and defined by the relative reflected photon flux per unit area), and total reflectance, $R_d$, as well as total transmittance, $T_B/T_0$, modify serially, during the course of aggregation. As mentioned earlier, for blood, total reflectance is given by: $R_d = (1+7\mu_a/\mu_s' + 3\sqrt{(3\mu_a/\mu_s'(1+\mu_a/\mu_s'))})^{-1}$. Given this expression, it is expected that $R_d$ decreased by reducing $\mu_s'$ during aggregation. Thus, in addition to measuring the platelet aggregate size through the analysis of the speckle fluctuations rate, OTEG may independently and in parallel track the rate and the scale of aggregation by following the changes in total reflectance measured for example by time-averaging of successive speckle frames. The DRP similarly measured from time-averaged speckle frames is given by:

$$R(\rho) = \frac{a'}{4\pi} \left[ \frac{1}{\mu_t'} \left( \mu_{eff} + \frac{1}{r_1} \right) \frac{e^{-\mu_{eff} r_1}}{r_1^2} + \left( \frac{1}{\mu_t'} + 2z_b \right) \left( \mu_{eff} + \frac{1}{r_2} \right) \frac{e^{-\mu_{eff} r_2}}{r_2^2} \right] \quad (5)$$

$$r_1^2 = \rho^2 + z_0^2, \, r_2^2 = \rho^2 + (z_0 + 2z_b)^2, \, z_b = 2A/\mu_t',$$

$$\mu_t' = \mu_a + \mu_s', \, \mu_{eff} = \sqrt{3\mu_a(\mu_a + \mu_s')} \, a' = \frac{\mu_s'}{\mu_a + \mu_s'}$$

where $z_0 = 1*_B$ (Blood transport mean free path), A is a parameter related to the relative refractive indices of the blood-air interface, $\mu_t'$ is the total interaction coefficient, a' is the scattering albedo, and $\mu_{eff}$ is the effective attenuation coefficient. When $\mu_s'$ reduces by aggregation, albedo, a', the effective attenuation coefficient, $\mu_{eff}$, and the total interaction coefficient, $\mu_t'$, all decrease. As a result, both the inset and logarithmic slope of DRP reduce. Changes in DRP profile provide additional independent measurement for the speed and the extent of aggregation.

When $\mu_s'$ reduces as a consequence of platelet aggregation, the transport mean free path of blood, $1*_B = 1/\mu_s'$ increases and the optical density of blood, i.e. its turbidity, is reduced. Thus, it is expected that the total transmittance of the blood increases as a consequence of platelet aggregation:

$$T_{Blood} = \frac{5l_B^*/3L}{(1 + 4l_B^*/3L)} \quad (6)$$

By tracking the total transmittance of the specimen, yet another reference is obtained for evaluating the speed and the scale of aggregation.

It is possible to plot the profile of $R_d(t)$, $T_{blood}(t)$, as well as R(0,t), i.e. DRP inset as a function of time, and $\partial \log(R(\rho,t))/\partial \rho|_{\rho 0}$, i.e. logarithmic slope of the DRP at a designated distance from the illumination center much like the aggregate size profile, a(t), and evaluate both the rate and the total extent of platelet aggregation, using either of these profiles.

Equivalently, it is possible to extract $1^*_B(t)$ from $T_{blood}(t)$ via eqn. (6) and express platelet aggregation in terms of the blood specimen optical density/turbidity, rather than the total transmittance.

The details of the process for evaluating the maxima/inset as well as the linear/log slope of DRP may be modified depending on the responsivity of the detector, solid angle of view, size of the region of interest (RoI), and the exposure/integration time, among other parameter. In particular, the slope of DRP may be evaluated by calculating the derivative, or by using linear/non-linear curve-fitting processes. Alternatively, both $\mu_a$ and $\mu_s'$ may be evaluated independently by fitting the radial profile of the DRP to eqn. (5). The $\mu_s'(t)$ may then serve as an substitute profile of platelet aggregation.

Platelet aggregation can be measured as above from reflected and transmitted speckle images. Platelets are blood cells that are of great importance in blood coagulation. Formation of a platelet plug at the site of injury is important in the coagulation response. During hemostasis, platelets are maintained in a resting state by endothelial inhibitory factors. The platelet plug is initiated by the exposure of collagen and local generation of thrombin. This causes normal platelets to adhere via collagen and von Willebrand factor (vWF) and further release additional platelet agonists such as thromboxane A2 and ADP. Platelet to platelet aggregation to form a platelet plug is then initiated by the activation of platelet surface integrins. In a variety of disease states or following acute trauma that cause hemorrhage, platelet function may be altered which may inhibit platelet aggregation resulting in uncontrolled bleeding. Alternatively, in thrombotic disease states characterized by hypercoagulability, platelet aggregation rate may be increased causing venous and arterial thrombosis which may be life threatening. Therefore, methods to measure platelet aggregation at the point of care enable the detection of defective platelet function and permit monitoring of antiplatelet agents to correct thrombotic states, or blood product transfusion to correct hemorrhagic conditions. Varying the amount of ADP is performed for validation purposes to show that our device is sensitive to differences in platelet aggregation caused by changing agonist concentration. For clinical use, a single concentration of ADP in the cartridge is sufficient.

FIG. 9A confirms that an OTEG device operable according to an embodiment of the invention can accurately measure changes in aggregate size of light scatterers induced by tuning concentration of $MgCl_2$ added to the suspensions of polystyrene beads (1.5 µm radius) to initiate clumping. The capability to detect platelet aggregation in ADP-activated blood and monitoring of such platelet aggregation was also verified via the experimental determination of the change of effective aggregate radius, as attested to by FIG. 9B. FIG. 9B displays, as but two experimental examples, the 5- and 2.5-fold growth of an aggregate radius of a blood-based scatterer with addition of 10 and 5 µM ADP relative to blood without ADP (a control sample). The effective aggregate radius increase with ADP concentration was detected with the OTEG device of the invention. Additionally, these results were verified via LTA conducted in the same samples.

To effectuate the steps of the embodiment 400 of an algorithm of the invention discussed above, and referring again to FIGS. 3A through 3C, the programmable electronic circuitry of the unit 330 is programmed to measure, based on the data output produced by the detector 316, a time-averaged total reflectance parameter characterizing the medium; to calculate, based on the total reflectance parameter, a mean square displacement associated with optical scatterers of the medium; and to produce an output representing a time-dependent product of a time-dependent effective radius of an optical scatterer of the medium and a viscoelastic modulus of the medium.

TABLE 2

Benchmark performance metrics for OTEG tool in Aim 1

| Performance Target | Expected value |
| --- | --- |
| Dimensions (radius × H) | 2" × 2" |
| Sample volume | <100 µL |
| Measurement temperature | 37° C. ± 1° C. |
| Field of View (FOV) | ~0.8 mm |
| Measurement depth | ~0.5 mm |
| Image transfer rate | 500 MB/s |
| Frame rate (100 × 100 pixels) | ~500 frames/s |
| Measurement Range | ~0.01 to 500 Pa |
| Accuracy | Correlation: R > 0.7, p < 0.05; & <10% deviation between OTEG and mechanical rheometer |
| Frequency range of ω | ~0.1 Hz-0.5 kHz |
| Data processing time/ data reporting interval | <30 s |
| Sensitivity (smallest measurable change in G*) | ~0.01 Pa (based on preliminary studies of glycerol dilutions - FIG. 7) |
| Precision/Reproducibility | ~90% |

Figure 3:
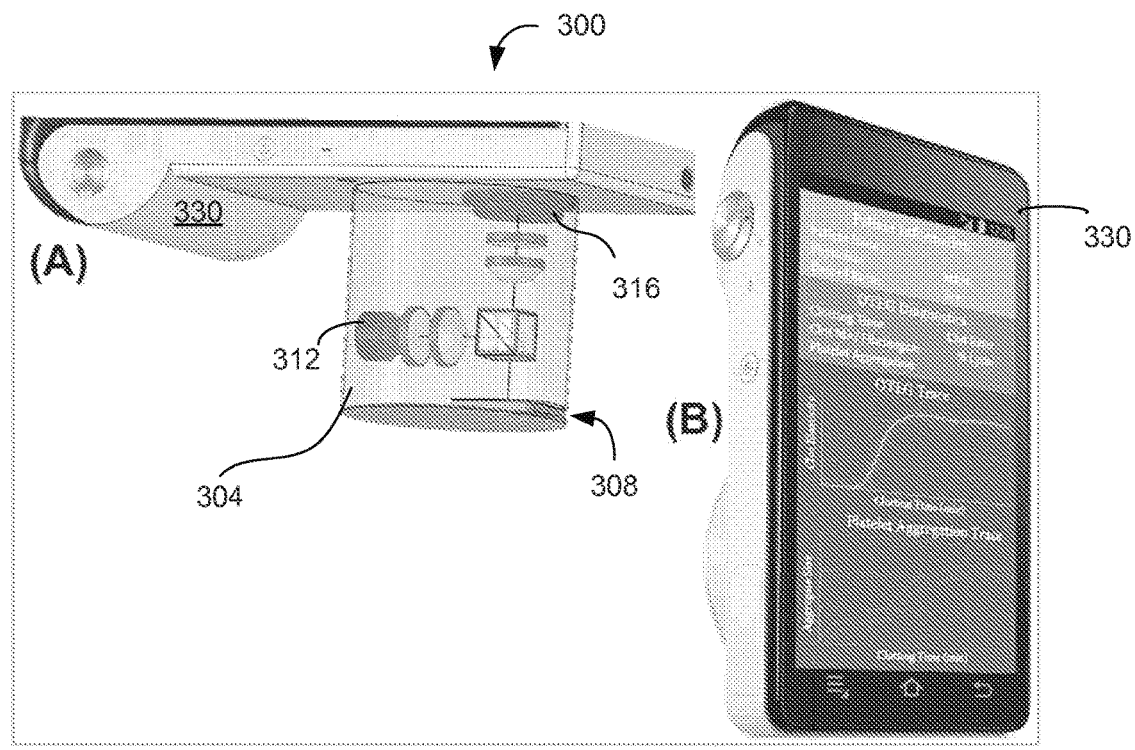
FIGS. 3A, 3B, and 3C illustrate schematically perspective views and an opto-electronic scheme of an embodiment of the optical thromboelastographer.
Figure 3:
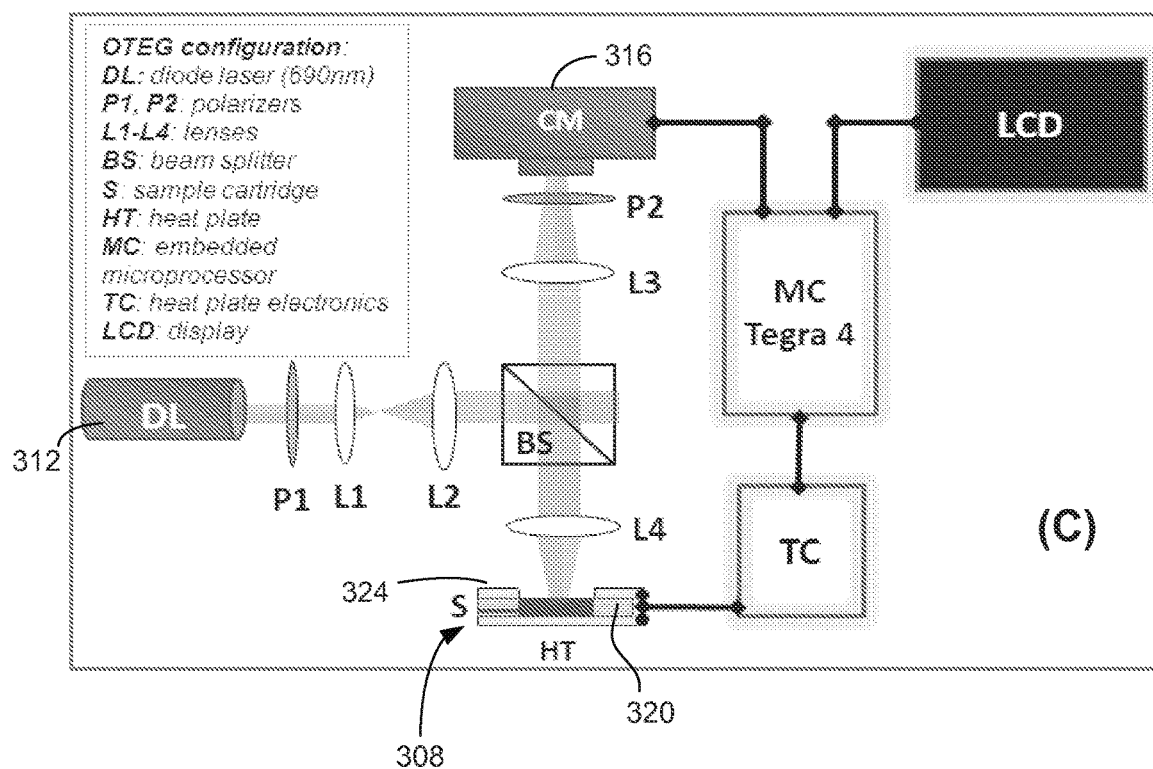

Table 2A above presents typical operational parameters for the embodiment 300 of FIG. 3.

Example 2

FIGS. 10A, 10B schematically illustrate a related embodiment 1000 of the device, shown as lensless, in which a laser diode 312 operates at 690 nm to illuminate the blood sample in the cartridge 308. Cross-polarized, transmitted light is detected by optionally passing such light through a pinhole array (or array of optical apertures) 1010 with a 32 element avalanche photodiode (APD) module 1014. While the use of a pinhole array facilitates a measurements of spatially coherent speckle to improve spatial contrast and reduces blurring in the data (which eventually may increase the background signal and reduce measurement sensitivity to noise), the measurement can generally be carried out and the device can be structured without the pinhole array. The APD output is sampled in parallel by a 32 channel DAQ card at a rate of 6.2K samples/s. The above components are assembled within a detachable housing 304 (3.0"×2.5"×1.0") interfaced via the USB port of the smartphone 1020 (such as, for example, the LG Nexus 5 phone powered by a quad-core 2.26 GHz microprocessor. A lock-in slot secures the blood cartridge in place over a custom heat plate. The optionally disposable cartridge may be pretreated with coagulation activators and platelet agonists (kaolin, tissue factor, ADP).

Figure 4B:
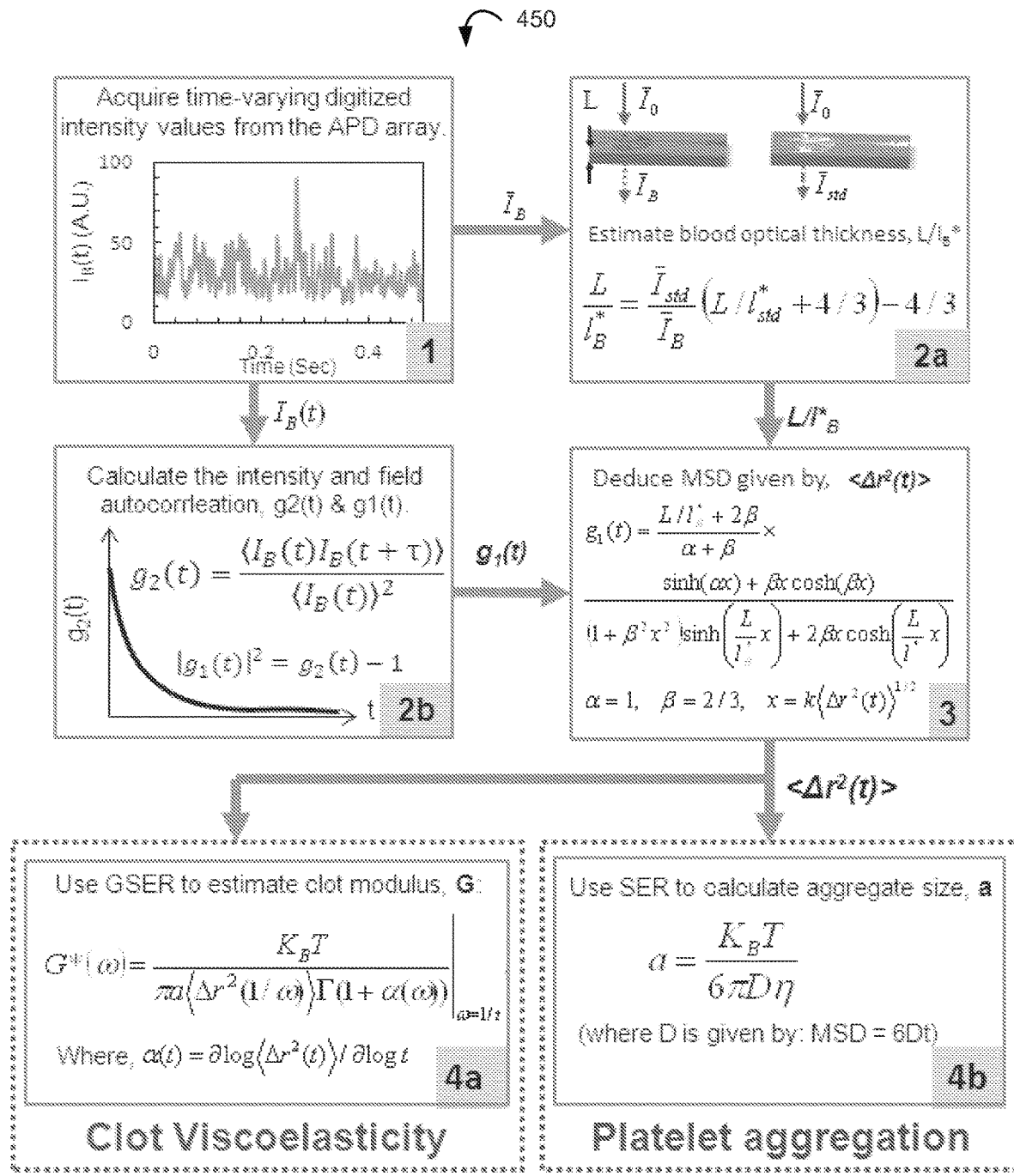
FIG. 4B is a flow-chart for a related embodiment of the OTEG algorithm. Box 1: Time-varying intensity, I(t), output of photodiodes are digitized at 6.2K samples/s by a DAQ card. Box 2: The I(t) time series is processed in two ways: (a) Time-averaged intensity provides the total transmitted intensity, $T_B$, which is compared with the total transmitted intensity of a standard sample of known transport mean free path, $l_{std}$ (i.e. polystyrene microspheres in water) to estimate the $L/l^*_B$ ratio. (b) Normalized intensity autocorrelation yields the $g_2(t)$ curve. Box 3: A closed form equation is used to estimate MSD from the measured $g_2(t)$ and $L/l^*_B$. Box 4: (a) The MSD is substituted in the Generalized Stokes-Einstein Relation (GSER) to yield the viscoelastic modulus of blood. (b) The effective scatter radius, a, is measured from the Stokes-Einstein relation (SER) to yield aggregate size in unclotted blood spiked with a platelet agonist. (D: diffusion coefficient, L: sample thickness).

FIG. 4B presents an alternative embodiment 450 of the algorithm according to which the optical data collected with the embodiment 1000 can be processed to obtain a multiplicity of blood-coagulation parameters at a bed-side in real time. Here, the transport mean free path, $1^*=1/\mu's$, is estimated from time-averaged light intensities [boxes 1,2] to obtain robust estimates of MSD and G(ω), as detailed below.

Estimating Transport Mean Free Path of Blood, $1_B^*$:

To estimate $1_B^*$, a onetime calibration is performed to evaluate the transmitted intensity, $I_{td}$, of a scattering standard of known $1^*_{std}$. Then the total intensity transmitted through blood, $I_B$, is calculated by temporal averaging of the intensity time series (over 1 second at a time, for example)

[box 2a], and $L/l_B^*$ is calculated using the equation in box 2a at each time point during coagulation. The total transmittance of the blood specimen, $T_{Blood}$, is given by the following equation:

$$T_{Blood} = \frac{I_B}{I_0} = \frac{5l_B^*/3L}{(1+4l_B^*/3L)} \quad (7)$$

Here, $I_0$ is the total incident intensity and $I_B$ is the total intensity that transmits through the blood. Moreover, $l^*_B$ is the transport mean free path of the blood and L is the length of the blood chamber. Evaluating the total transmittance might be subject to errors induced by changes within the incident intensity profile or other experimental factors. Therefore, often a standard calibration sample of known total transmittance, $T_{std}$, and transport mean free path, $l^*_{std}$, is used to calibrate the OTEG measurements of total transmittance and blood turbidity, as well as the blood transport mean free path, $l^*_B$. The total transmittance of this standard sample is given by:

$$T_{std} = \frac{I_{std}}{I_0} = \frac{5l_{std}^*/3L}{1+4l_{std}^*/3L} \quad (8)$$

Thus, the ratio of the blood to standard sample total transmittance is given by:

$$\frac{T_{std}}{T_{Blood}} = \frac{l_{std}^*(3L+4l_{Blood}^*)}{l_{Blood}^*(3L+4l_{std}^*)} \quad (9)$$

Substituting Eqs. (7) and (8) for the total transmittance in the Eq. (9), and rearranging the parameters yields the following expression for the blood transport mean free path, $l^*_B$:

$$\frac{L}{l_B^*} = \frac{\bar{I}_{std}(3L+4l_{std}^*)}{3\bar{I}_B l_{std}^*} - \frac{4}{3} \quad (10)$$

Here, L is the length of the blood chamber, $\bar{I}_{std}$ is the average intensity that passes through the standard calibrating sample, and is measured apriori. $\bar{I}_B$ is the average intensity that transmits through the blood sample and is measured in real-time during the course of aggregation/coagulation. Moreover, $l^*_{std}$ is the transport mean free path of the calibrating samples. The $L/l^*_B$ may then be directly replaced in the $g_2(t)$ expression, displayed flowchart of FIG. 4B and also reiterated in Eq. (4).

Estimating MSD and Clot Viscoelasticity, G:

First, to calculate the MSD, $g_2(t)$ is measured via the normalized autocorrelation of the light intensity time trace [box 2b]. Then, $l_B^*$ estimated above, is replaced in box 3, and the value of MSD is extracted. The modulus $G(\omega)$ is then calculated via the GSER [box 4a]. The measurement $G=aG(\omega')$, representing the modulus scaled by a at a single frequency, $\omega=\omega'$, is further determined as discussed in reference to FIG. 4A.

Deriving Blood Coagulation Parameters from the Clot Viscoelasticity Trace:

To obtain the clot viscoelasticity trace, the modulus, G, is measured as above, and the change in G during clotting relative to whole blood (at time=0) is sampled every 20 s, for example, to describe the time-course of blood coagulation.

The assessment of platelet aggregation is carried out in a fashion similar to that described in reference to the embodiment 400 of FIG. 4A.

To effectuate the steps of the embodiment 450 of the algorithms of the invention, the programmable electronic circuitry of the unit 330 is specifically programmed at least to measure, based on the data output from the detector 316, an optical thickness of the medium within the chamber; to calculate, on said optical thickness and an autocorrelation function of the cross-polarized speckle pattern, a mean square displacement associated with optical scatterers of the medium; and to produce an output representing, when the medium includes a stationary sample of blood, a platelet aggregation function and at least first and second parameters including a clotting time, a rate of clot formation, a clot strength, and a fibrinolysis function.

TABLE 2

Optical coagulation sensor performance benchmarks

| Performance Target | Expected value |
|---|---|
| Dimensions (L × W × H) | 3.0" × 2.5" × 1.0" |
| Sample volume | ~50 µL |
| Measurement temperature | 37° C. ± 1° C. |
| Measurement area | ~4 mm |
| Measurement depth | ~1.0 mm |
| Sampling rate | 6.2K samples/s |
| Measurement Range | ~0.01 to 500 Pa |
| Accuracy | Correlation: R > 0.7, p < 0.05; & <10% deviation between optical sensor and mechanical rheometer |
| Data processing/reporting interval during coagulation | <20 s |
| Sensitivity (smallest measurable change in G*) | ~0.01 Pa (based on preliminary studies of glycerol dilutions - FIG. 7) |
| Precision/Reproducibility | ~90% |

Figure 10:
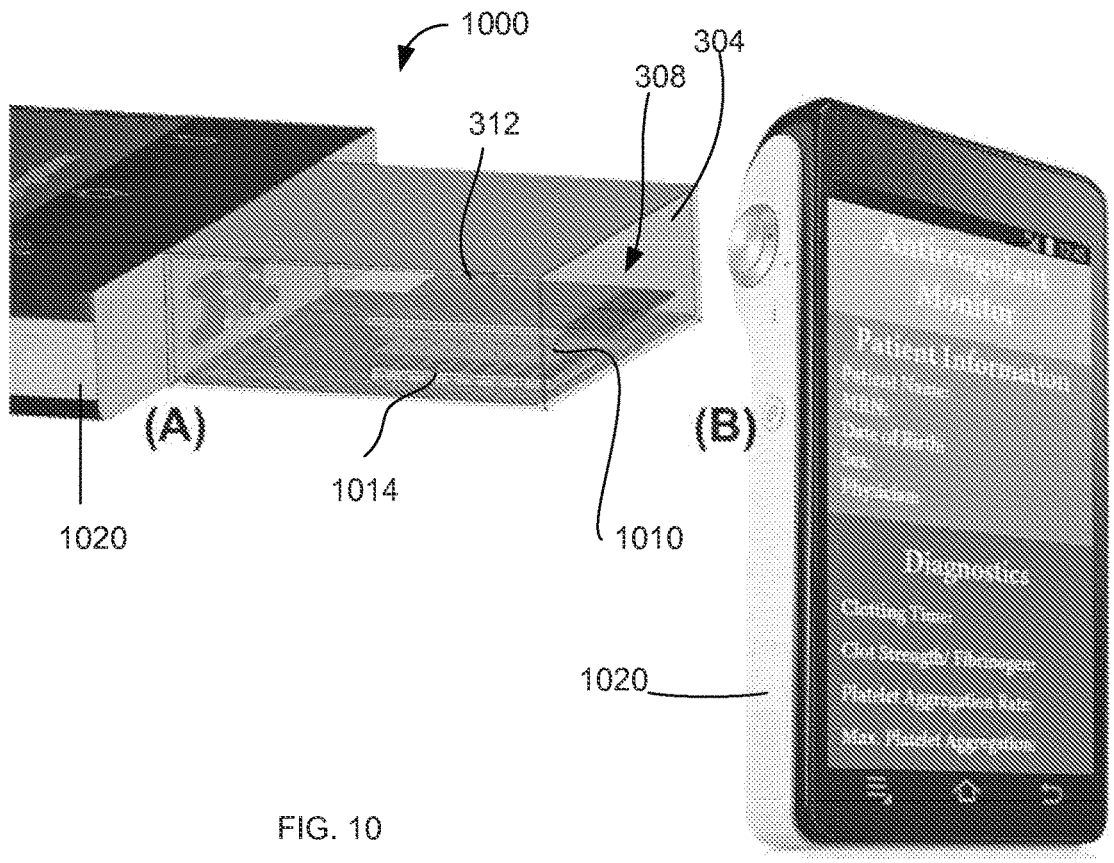
FIGS. 10A and 10B illustrate a related embodiment of the device of the invention.

Table 2B above presents target operational parameters (expected values of performance targets, including sampling rate, measurement range, accuracy and sensitivity) for the embodiment 1000 of FIG. 10.

It is appreciated that embodiments of the invention provide enablement of a goal-directed transfusion or anti-thrombotic therapy. Indeed, rapid coagulation profiling using OTEG would play a crucial role to tailor therapy based on the actual needs of each patient, reducing the risks of inappropriate transfusion or anti-thrombotic therapy. This 'theranostic' potential offered by OTEG has several advantages. Resuscitation following bleeding often involves transfusion of fresh frozen plasma (FFP) and packed RBCs (pRBC) in a fixed ratio to replace blood volume and clotting factors. Higher volumes of pRBC may aggravate dilutional coagulopathy, while high volumes of FFP may cause respiratory distress. In contrast to a fixed FFP:pRBC ratio, goal-directed transfusion informed by OTEG would significantly improve patient outcome. OTEG monitoring would permit individualized transfusion protocols based on real-time test results, to guide blood component supplementation to correct specific defects in the coagulation cascade. For instance, long R times may indicate need for clotting factors, reduced MA and a may warrant fibrinogen replacement, increased % LY (hyperfibrinolysis) may suggest need for anti-fibrinolytic therapy and low platelet aggregation may require platelet replacement. In hypercoagulable patients at increased thrombotic risk, OTEG could inform the appropriate anti-coagulant or anti-platelet therapy.

Figure 11:
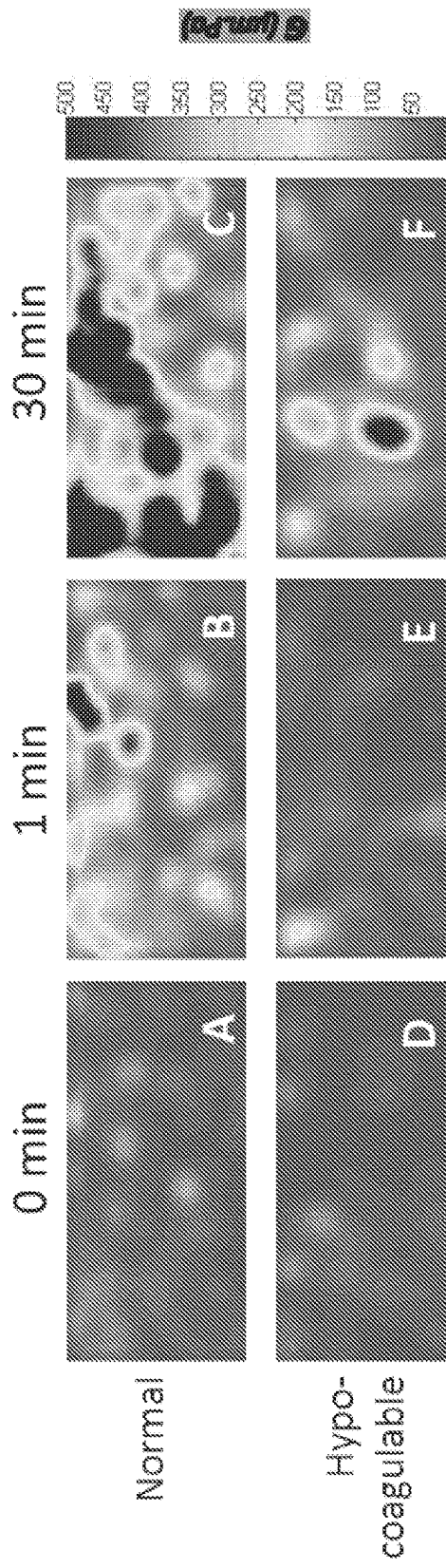
FIG. 11 shows OTEG 2D viscoelasticity maps from normal (top row) and hypo-coagulable patients (bottom row), demonstrating the high sensitivity of the OTEG device in detecting very early formation of 'micro-clots'. Even at 1 min differences in the rate of clot formation are detected between normal and hypo-coagulable states.

In reference to FIG. 11, the operation of the embodiment of the invention achieves a rather substantial experimental measurement sensitivity of ~0.01 Pa in detecting small changes in clot viscoelasticity, which allows micro-clot formations to be detected and spatially mapped very early in the coagulation process, in less than half the time required for the same detection by the TEG modality, with the use of, for example, embodiment 300 of FIGS. 3A, 3B, 3C. As mentioned above very small micro-clots can be detected with high micromechanical sensitivity, and, as a result, the OTEG device can measure blood clot formation in a matter of just a few minutes (for example, 1 to 5 minutes) in advantageous contradistinction with 5 to 20 minutes required by a mechanical system such as TEG and ROTEM. In addition, while the conventional TEG device employed in related art averages over the entire sample (because it employs stirring of the blood sample), an OTEG embodiment of the present invention is operable to image speckle patterns, and, as a result, spatio-temporal analysis of the speckle pattern can be conducted with micromechanical sensitivity.

Figure 12:
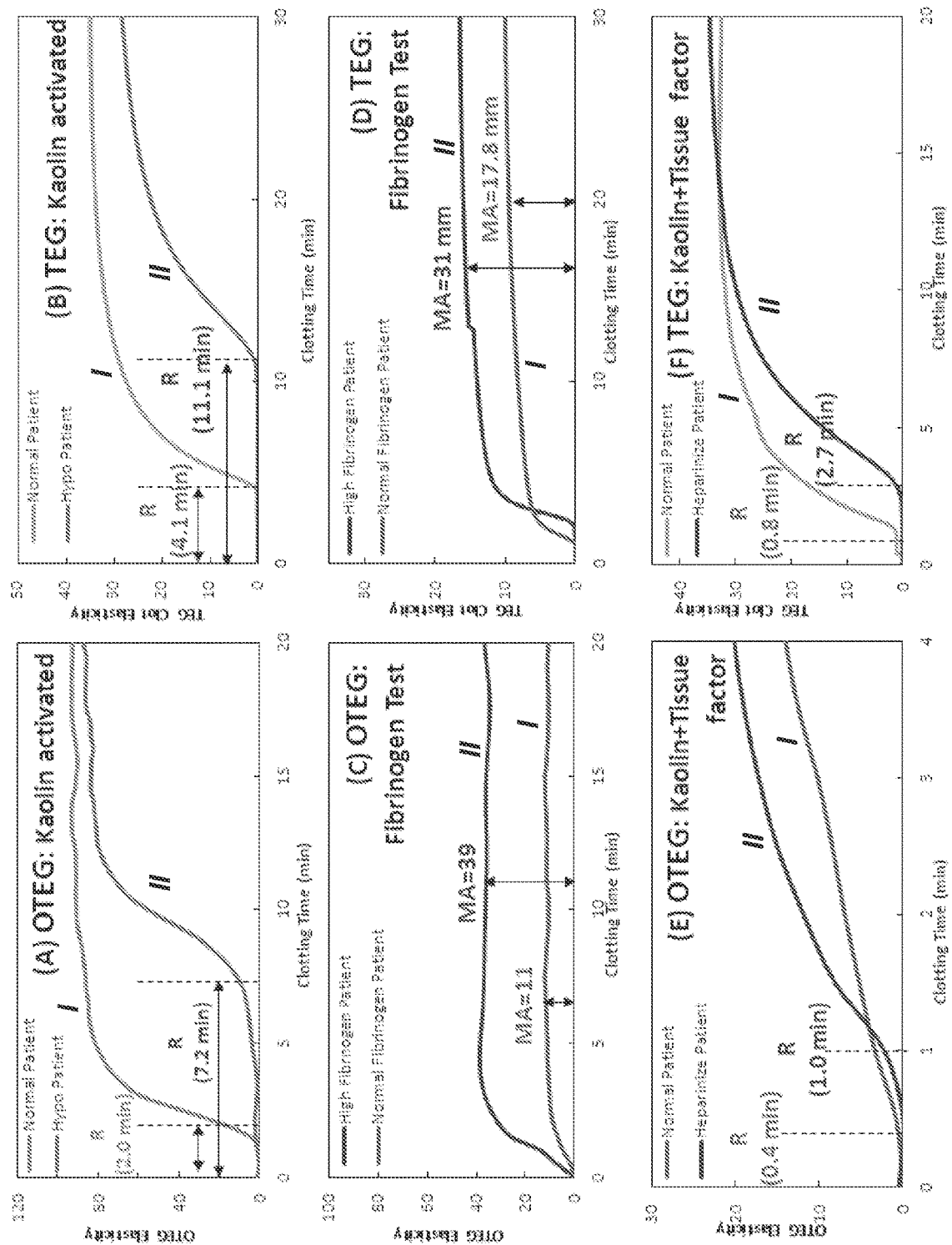
FIG. 12 illustrates the comparison between blood viscoelasticity curves obtained using an OTEG embodiment of the invention (left column, plots A, C, E) and conventional TEG approach (right column, plots B, D, F) using different functional assays.

FIG. 12 (plots A, B, C, D, E, and F) schematically illustrate the results of preliminary studies conducted with the use of the existing bench-top OTEG in comparison with the results of corresponding TEG analysis (used as a standard reference). Normal coagulation status in 3 patients (curves I) is compared with 3 patients with coagulation defects (curves II). Plot A: using standard Kaolin assay, OTEG accurately detects increased R-time and lower clot strength (MA) in hypocoagulable versus normal blood. Plot C: using functional fibrinogen assay, OTEG accurately measures increased clot strength (MA) due to increased fibrinogen levels. Plot D: Adding tissue factor to Kaolin significantly shortens clotting time via activating both the intrinsic and extrinsic pathways and is accurately detected by OTEG as is noted by comparing R-times in plots A and C. In all cases, OTEG results closely correlate with corresponding TEG results shown in plots B, D and F. The results presented in FIG. 12 attest to the fact that an OTEG embodiment of the invention is operable to provide coagulation data similar to those conventionally received with the use of a TEG modality, but optically, using minute sample volumes, within about $1/4^{th}$ of the time, and at a hundredth of the cost associated with the TEG measurement.

To effect the operation of an embodiment of the above-described OCS (OTEG) optical thromboelastographer system and performance of the steps required to acquire and process the laser-speckle data representing results of the measurements of the sample(s) contained in the cartridge, the system may require the operation of a computer processor controlled by application-specific instructions stored in a tangible memory element. Those skilled in the art should readily appreciate that required algorithmical functions, operations, and decisions may be implemented as computer program instructions, software, hardware, firmware or combinations thereof. Those skilled in the art should also readily appreciate that instructions or programs defining the functions and elements of the present invention may be delivered to a processor in many forms, including, but not limited to, information permanently stored on non-writable storage media (e.g. read-only memory devices within a computer, such as ROM, or devices readable by a computer I/O attachment, such as CD-ROM or DVD disks), information alterably stored on writable storage media (e.g. floppy disks, removable flash memory and hard drives) or information conveyed to a computer through communication media, including wired or wireless computer networks. In addition, while the invention may be embodied in software, the functions necessary to implement the invention may optionally or alternatively be embodied in part or in whole using firmware and/or hardware components, such as combinatorial logic, Application Specific Integrated Circuits (ASICs), Field-Programmable Gate Arrays (FPGAs) or other hardware or some combination of hardware, software and/or firmware components.

References made throughout this specification to "one embodiment," "an embodiment," "a related embodiment," or similar language mean that a particular feature, structure, or characteristic described in connection with the referred to "embodiment" is included in at least one embodiment of the present invention. Thus, appearances of these phrases and terms may, but do not necessarily, refer to the same implementation. It is to be understood that no portion of this disclosure, taken on its own and in possible connection with a figure, is intended to provide a complete description of all features of the invention.

In addition, the following disclosure may describe features of the invention with reference to corresponding drawings, in which like numbers represent the same or similar elements wherever possible. It is understood that in the drawings, the depicted structural elements are generally not to scale, and certain components may be enlarged relative to the other components for purposes of emphasis and clarity of understanding. It is also to be understood that no single drawing is intended to support a complete description of all features of the invention. In other words, a given drawing is generally descriptive of only some, and generally not all, features of the invention. A given drawing and an associated portion of the disclosure containing a description referencing such drawing do not, generally, contain all elements of a particular view or all features that can be presented is this view, for purposes of simplifying the given drawing and discussion, and to direct the discussion to particular elements that are featured in this drawing. A skilled artisan will recognize that the invention may possibly be practiced without one or more of the specific features, elements, components, structures, details, or characteristics, or with the use of other methods, components, materials, and so forth. Therefore, although a particular detail of an embodiment of the invention may not be necessarily shown in each and every drawing describing such embodiment, the presence of this detail in the drawing may be implied unless the context of the description requires otherwise. In other instances, well known structures, details, materials, or operations may be not shown in a given drawing or described in detail to avoid obscuring aspects of an embodiment of the invention that are being discussed. Furthermore, the described single features, structures, or characteristics of the invention may be combined in any suitable manner in one or more further embodiments.

Moreover, in the schematic logical flow chart or process is discussed, the depicted order of the logical flow and/or processing or method steps may be indicative of only a specific embodiment of the presented method. Other steps and methods may be conceived that are equivalent in function, logic, or effect to one or more steps, or portions thereof, of the illustrated method, unless stated otherwise.

The invention as recited in claims appended to this disclosure is intended to be assessed in light of the disclosure as a whole, including features disclosed in prior art to which reference is made.

The disclosed embodiments of the invention disclose general OTEG-concepts according to the invention and discuss specific examples of performing simultaneous photometric measurements in a consolidated package. The embodiment of the system shown in FIG. 3A, 3B, 3C is operable to generate the required coagulation-related information while utilizing only a few drops of blood (approximately 100 µL or generally in the amount not exceeding 100 microliters), while the embodiment discussed in reference to FIGS. 10A, 10B uses only a single blood drop that can just obtained via a finger stick. Overall, the devices of the invention are operable to measure multiple parameters, clotting time, clot formation rate, clot strength, fibrinolysis, and platelet aggregation using just 1-2 drops of blood thereby facilitating the home (point-of-care) use. This is in stark contradistinction with the conventionally employed TEG/ROTEM systems that generally require >300 µL from a venipuncture-based venous blood draw to provide the coagulation data, and are not operable with the specified minute quantities of blood. Modifications to, and variations of, the illustrated embodiments may be made without departing from the inventive concepts disclosed herein. Furthermore, disclosed aspects, or portions of these aspects, may be combined in ways not listed above. Accordingly, the invention should not be viewed as being limited to the disclosed embodiment(s). In addition, the terminology used herein is with the purpose of describing particular embodiments only, and is not intended to limit the scope of the present invention.

The invention claimed is:

1. A hand-held optical thromboelastographer operable at a point-of-care, comprising:
    an assembly including a housing unit that contains
        a base substrate defining a void therein and having a first surface with an aperture providing access to said void, the base substrate being removably reinsertable into the housing unit;
        a superstrate juxtaposed with the first surface over the aperture to form a closed chamber including the void such as to prevent access to said chamber through the aperture; and
        a detector disposed to acquire light scattered by a medium within the chamber through the superstrate and to provide a data output representing a cross-polarized speckle pattern generated by the medium; and
    a hand-held data-processing unit that includes electronic circuitry that is in operable communication with the detector and that is programmed to:
        measure, based on the data output, a time-averaged total reflectance parameter and an autocorrelation function of the cross-polarized speckle pattern;
        calculate, based on the autocorrelation function of the cross-polarized speckle pattern, a mean square displacement associated with optical scatterers of the medium;
        estimate, at a selected frequency or for a selected time interval, a time-dependent viscoelastic modulus of the medium; and
        produce, based on at least one of the time-dependent viscoelastic modulus and mean square displacement of the medium, an output representing at least two blood coagulation parameters selected from the group consisting of:
            a clotting time,
            a clot rate,
            a time-dependent effective radius of the optical scatterers of the medium, and
            a maximum viscoelastic modulus of the medium.

2. An optical thromboelastographer according to claim 1, wherein the medium includes a stationary sample of blood, and wherein the assembly is removably attachable to the hand-held data-processing unit to perform testing of a viscoelasticity of the stationary sample of blood at a point-of-care.

3. An optical thromboelastographer according to claim 2, wherein the stationary sample of blood is in an amount not exceeding 100 µL.

4. An optical thromboelastographer according to claim 2, wherein the selected frequency or the selected time interval is defined to maximize a correlation between a blood-coagulation parameter derived from the time-dependent viscoelastic modulus of the medium and a reference coagulation parameter obtained with the use of a mechanical thromboelastographer.

5. An optical thromboelastographer according to claim 1, wherein the electronic circuitry is further programmed to determine the viscoelastic modulus of the medium corrected for changes of at least one of an optical absorption and an optical scattering of the medium.

6. An optical thromboelastographer according to claim 1, further comprising a vibration-isolating platform operable to compensate for a relative movement between the base substrate and the housing unit.

7. A hand-held optical thromboelastographer operable at a point-of-care, comprising:
    an assembly including a housing unit that contains
        a sample cartridge having a chamber in a plane-parallel substrate, said chamber being optically accessible through a superstrate sealingly overlaying the chamber, said chamber being fluidly accessible through a channel, said cartridge being removably reinsertable into the housing unit;
        an optical train transmitting light that has traversed said chamber, the optical train devoid of optical power and including an array of optical apertures; and
        a detector disposed to acquire light scattered by a medium within the chamber through the array of optical apertures and to provide a data output representing a cross-polarized speckle pattern generated by the medium;
    a hand-held data-processing unit that includes electronic circuitry that is in operable communication with the detector and that is programmed to:
        measure, based on the data output, a time-averaged total reflectance parameter and an autocorrelation function of the cross-polarized speckle pattern;
        calculate, based on the autocorrelation function of the cross-polarized speckle pattern, a mean square displacement associated with optical scatterers of the medium;
        estimate, at a selected frequency or for a selected time interval, a time-dependent viscoelastic modulus of the medium; and
        produce, based on at least one of the time-dependent viscoelastic modulus and mean square displacement of the medium, an output representing a platelet aggregation function and at least first and second blood coagulation parameters selected from the group consisting of:
            a clotting time,
            a rate of clot formation,
            a clot strength, a fibrinolysis function;
a time-dependent effective radius of the optical scatterers of the medium; and
a maximum viscoelastic modulus of the medium; and
an output device operably cooperated with the electronic circuitry to display a visually-perceivable representation of the output, said assembly being removably attached to the output device during operation of the optical thromboelastographer.

8. An optical thromboelastographer according to claim 7, wherein the medium includes a stationary sample of blood.

9. An optical thromboelastographer according to claim 8, wherein the viscoelastic modulus of the medium is corrected for changes of at least one of an optical absorption and an optical scattering of the medium.

10. An optical thromboelastographer according to claim 8, wherein the stationary sample of blood is in an amount not exceeding 100 µL.

11. An optical thromboelastographer according to claim 8, wherein the selected frequency or the selected time interval is defined to maximize a correlation between a blood-coagulation parameter derived from the time-dependent viscoelastic modulus of the medium and a reference coagulation parameter obtained with the use of a mechanical thromboelastographer.

\* \* \* \* \*